United States Patent
Schafer et al.

(10) Patent No.: US 9,649,396 B2
(45) Date of Patent: May 16, 2017

(54) METHODS, DEVICES, AND SYSTEMS FOR TREATING BACTERIA WITH MECHANICAL STRESS ENERGY AND ELECTROMAGNETIC ENERGY

(71) Applicant: Photosonix Medical, Inc., Ambler, PA (US)

(72) Inventors: Mark E. Schafer, Lower Gwynedd, PA (US); Tessie Brown McNeely, Gwynedd Valley, PA (US)

(73) Assignee: PHOTOSONIX MEDICAL, INC., Ambler, PA (US)

( * ) Notice: Subject to any disclaimer, the term of this patent is extended or adjusted under 35 U.S.C. 154(b) by 0 days.

(21) Appl. No.: 14/665,074

(22) Filed: Mar. 23, 2015

(65) Prior Publication Data

US 2015/0283277 A1     Oct. 8, 2015

Related U.S. Application Data

(60) Provisional application No. 61/975,341, filed on Apr. 4, 2014.

(51) Int. Cl.
*A61L 2/025*      (2006.01)
*A61L 2/08*       (2006.01)
(Continued)

(52) U.S. Cl.
CPC ............... *A61L 2/025* (2013.01); *A61C 17/00* (2013.01); *A61L 2/00* (2013.01); *A61L 2/08* (2013.01);
(Continued)

(58) Field of Classification Search
CPC ............. A61L 2/025; A61L 2/088; A61L 2/24
See application file for complete search history.

(56) References Cited

U.S. PATENT DOCUMENTS

| 2,283,285 A | 5/1942 | Pohlman |
| 2,830,578 A | 4/1958 | DeGroff |

(Continued)

FOREIGN PATENT DOCUMENTS

| CA | 2268415 A1 | 10/2000 |
| WO | 2007050144 A1 | 5/2007 |

OTHER PUBLICATIONS

International Searching Authority, International Search Report and Written Opinion issued in corresponding Application No. PCT/US2015/021998, dated Jul. 8, 2015, 13 pages.

(Continued)

*Primary Examiner* — Sean E Conley
(74) *Attorney, Agent, or Firm* — Thompson Hine LLP

(57) ABSTRACT

A portion of a treatment device for treating bacteria may be coupled with the bacteria through direct or indirect contact. Mechanical stress energy and electromagnetic energy are generated with the treatment device, and are transmitted from the treatment device to the bacteria during the coupling. The bacteria are treated with both the mechanical stress energy and the electromagnetic energy to produce a killing effect on the bacteria. A treatment device may include a mechanical stress energy emitting portion, an electromagnetic energy emitting portion, and a contacting portion for coupling into direct or indirect contact with the bacteria and transmitting mechanical stress energy to the bacteria during the coupling. The mechanical stress energy emitting portion and the electromagnetic energy emitting portion are operable to treat the bacteria with a combination of mechanical stress energy and electromagnetic energy to produce a killing effect on the bacteria.

17 Claims, 15 Drawing Sheets

(51) Int. Cl.
<table>
<tr><td>A61L 2/24</td><td>(2006.01)</td></tr>
<tr><td>A61C 17/00</td><td>(2006.01)</td></tr>
<tr><td>A61N 7/00</td><td>(2006.01)</td></tr>
<tr><td>A61L 2/00</td><td>(2006.01)</td></tr>
<tr><td>A61L 9/00</td><td>(2006.01)</td></tr>
<tr><td>A61B 18/00</td><td>(2006.01)</td></tr>
<tr><td>A61N 5/06</td><td>(2006.01)</td></tr>
</table>

(52) U.S. Cl.
CPC .............. *A61L 2/088* (2013.01); *A61L 2/24* (2013.01); *A61L 9/00* (2013.01); *A61N 5/0624* (2013.01); *A61N 7/00* (2013.01); *A61B 2018/00994* (2013.01); *A61N 5/0601* (2013.01); *A61N 5/0616* (2013.01); *A61N 2005/0606* (2013.01); *A61N 2005/0644* (2013.01); *A61N 2005/0662* (2013.01); *A61N 2007/0034* (2013.01); *A61N 2007/0078* (2013.01)

(56) References Cited

U.S. PATENT DOCUMENTS

| | | |
|---|---|---|
| 3,358,677 A | 12/1967 | Sheldon |
| 3,602,577 A | 8/1971 | Byram |
| 3,828,769 A | 8/1974 | Mettler |
| 4,412,148 A | 10/1983 | Klicker et al. |
| 4,530,360 A | 7/1985 | Duarte |
| 4,658,176 A | 4/1987 | Nakaya et al. |
| 4,683,396 A | 7/1987 | Takeuchi et al. |
| 4,930,504 A | 6/1990 | Diamantopoulos et al. |
| 5,259,380 A | 11/1993 | Mendes et al. |
| 5,316,000 A | 5/1994 | Chapelon et al. |
| 5,358,503 A | 10/1994 | Bertwell et al. |
| 5,520,612 A | 5/1996 | Winder et al. |
| 5,549,544 A | 8/1996 | Young et al. |
| 5,690,608 A | 11/1997 | Watanabe et al. |
| 5,699,804 A | 12/1997 | Rattner |
| 5,913,883 A | 6/1999 | Alexander et al. |
| 6,273,864 B1 | 8/2001 | Duarte et al. |
| 6,290,713 B1 | 9/2001 | Russell |
| 6,361,509 B1 | 3/2002 | Reuner |
| 6,398,753 B2 | 6/2002 | McDaniel |
| 6,443,978 B1 | 9/2002 | Zharov |
| 6,533,803 B2 | 3/2003 | Babaev |
| 6,702,749 B2 | 3/2004 | Paladini et al. |
| 6,761,729 B2 | 7/2004 | Babaev |
| 7,022,089 B2 | 4/2006 | Ooba et al. |
| 7,090,649 B2 | 8/2006 | Kang |
| 7,195,603 B2 | 3/2007 | Yamazaki et al. |
| 7,273,459 B2 | 9/2007 | Desilets et al. |
| 7,282,036 B2 | 10/2007 | Masuda |
| 8,206,326 B2 | 6/2012 | Schafer et al. |
| 8,523,791 B2 | 9/2013 | Caster |
| 8,574,174 B2 | 11/2013 | Schafer et al. |
| 9,061,128 B2 | 6/2015 | Hall et al. |
| 2003/0032900 A1 | 2/2003 | Ella |
| 2003/0153961 A1 | 8/2003 | Babaev |
| 2004/0077977 A1 | 4/2004 | Ella et al. |
| 2004/0236252 A1 | 11/2004 | Muzzi et al. |
| 2005/0049543 A1 | 3/2005 | Anderson et al. |
| 2005/0137656 A1 | 6/2005 | Malak |
| 2005/0196725 A1 | 9/2005 | Fu |
| 2006/0184074 A1 | 8/2006 | Vaezy et al. |
| 2008/0221491 A1 | 9/2008 | Slayton et al. |
| 2009/0163964 A1 | 6/2009 | Boyden et al. |
| 2009/0227909 A1 | 9/2009 | Schafer et al. |
| 2010/0160838 A1 | 6/2010 | Krespi |
| 2011/0184499 A1 | 7/2011 | Radi |
| 2012/0029394 A1 | 2/2012 | Babaev |
| 2012/0209151 A1 | 8/2012 | Zhou et al. |
| 2014/0058296 A1 | 2/2014 | Schafter et al. |
| 2014/0276247 A1 | 9/2014 | Hall et al. |
| 2014/0378873 A1* | 12/2014 | Chernomorsky ........ A61N 7/00 601/2 |
| 2015/0079655 A1* | 3/2015 | Laugharn, Jr. ......... B01D 43/00 435/173.7 |
| 2015/0100002 A1 | 4/2015 | Choi |

OTHER PUBLICATIONS

United States Patent and Trademark Office, International Search Report and Written Opinion for PCT/US/2009/035816, dated Apr. 21, 2009 (9 pages).

Newnham, R.E., et al., "Composite Piezoelectric Transducers," Materials in Engineering, vol. 2, Dec. 1980, pp. 83-106 (14 pages).

The International Bureau of WIPO, International Preliminary Report on Patentability issued in International Application No. PCT/US2015/021998 dated Oct. 4, 2016.

European Patent Office, International Search Report and Written Opinion issued in International Application No. PCT/US16/27396 dated Mar. 28, 2017.

* cited by examiner

| Subject | Exposure Time | Ultrasound PRF | Bacterial Reduction |
|---------|---------------|----------------|---------------------|
| 1 | 20 min | 100 Hz | 80% |
| 2 | 60 min | 100 Hz | 95% |
| 3 | 60 min | 100 Hz | 97% |
| 4 | 60 min | 100 Hz | 53% |
| 5 | 60 min | 100 Hz | 72% |
| 6 | 30 min | 200 Hz | 98% |
| 7 | 30 min | 200 Hz | 92% |
| 8 | 15 min | 200 Hz | 92% |

US 9,649,396 B2

METHODS, DEVICES, AND SYSTEMS FOR TREATING BACTERIA WITH MECHANICAL STRESS ENERGY AND ELECTROMAGNETIC ENERGY

CROSS-REFERENCE TO RELATED APPLICATIONS

This application claims the benefit of U.S. Provisional Application Ser. No. 61/975,341, filed Apr. 4, 2014 (pending), the disclosure of which is hereby incorporated by reference herein in its entirety.

BACKGROUND

The present invention relates generally to treatment of bacteria and, more particularly, to methods, devices, and systems for treating bacteria.

Bacteria, including bacterial biofilms, have a widespread presence on living and non-living surfaces alike, including human skin, prosthetic implants, medical catheters, shower drains, piping, watercraft hulls, and any other surface exposed to an aqueous environment in which microorganisms are generally present. Bacterial biofilm formation begins when free-floating bacteria cells, referred to as planktonic cells, adhere to a hydrated surface. The anchored bacteria cells, referred to as sessile cells, mature and colonize on the surface and may spread to additional surfaces through dispersion, thereby growing the biofilm.

Bacteria growing on or around human tissue may pose various health risks, such as skin disease. In this regard, it is desirable to treat such bacteria in a manner that is effective to disrupt and thereby destroy the bacteria without harming the human tissue itself. However, as bacteria grows and matures, for example into a biofilm, it may become increasingly resistant to traditional antibiotic treatments. Ultrasound has been consulted as a possible alternative means for treating bacteria. While testing has revealed that high intensities of ultrasound prove effective against bacteria, including bacterial biofilms, such intensities are generally hazardous to human tissue and thus are impractical for clinical treatments on patients.

Accordingly, there remains a need for an effective treatment against bacteria beyond conventional antibiotics, where the treatment is also safe for use on human tissue.

SUMMARY

An exemplary method for treating bacteria may include coupling a portion of a treatment device with the bacteria through direct or indirect contact, generating mechanical stress energy with the treatment device, and generating electromagnetic energy with the treatment device. The mechanical stress energy and the electromagnetic energy may be transmitted from the treatment device to the bacteria during the coupling with the bacteria. The bacteria may be treated with both the mechanical stress energy and the electromagnetic energy generated by the treatment device to produce a killing effect on the bacteria.

An exemplary treatment device for treating bacteria may include a mechanical stress energy emitting portion operable to generate mechanical stress energy, and an electromagnetic energy emitting portion operable to generate electromagnetic energy. The treatment device may further include a contacting portion configured to be coupled into direct or indirect contact with the bacteria and to transmit at least the mechanical stress energy to the bacteria during the coupling. The mechanical stress energy emitting portion and the electromagnetic energy emitting portion may be operable to treat the bacteria with a combination of the mechanical stress energy and the electromagnetic energy to produce a killing effect on the bacteria.

BRIEF DESCRIPTION OF THE SEVERAL VIEWS OF THE DRAWINGS

The accompanying drawings, which are incorporated in and constitute a part of this specification, illustrate embodiments of the invention and, together with a general description of the invention given above, and the detailed description of the embodiments given below, serve to explain the principles of the invention.

DETAILED DESCRIPTION

Referring to the figures, various embodiments for treating bacteria (e.g., bacterial biofilms, which is one example used in the description below) with combined mechanical stress energy, such as ultrasound, and electromagnetic energy, such as light, are described below. It will be understood that other types of mechanical stress energy and electromagnetic energy may be used in other treatment settings and embodiments consistent with this disclosure, but the exemplary embodiments below generally refer to ultrasound and light for the sake of simplicity.

Figure 1A:
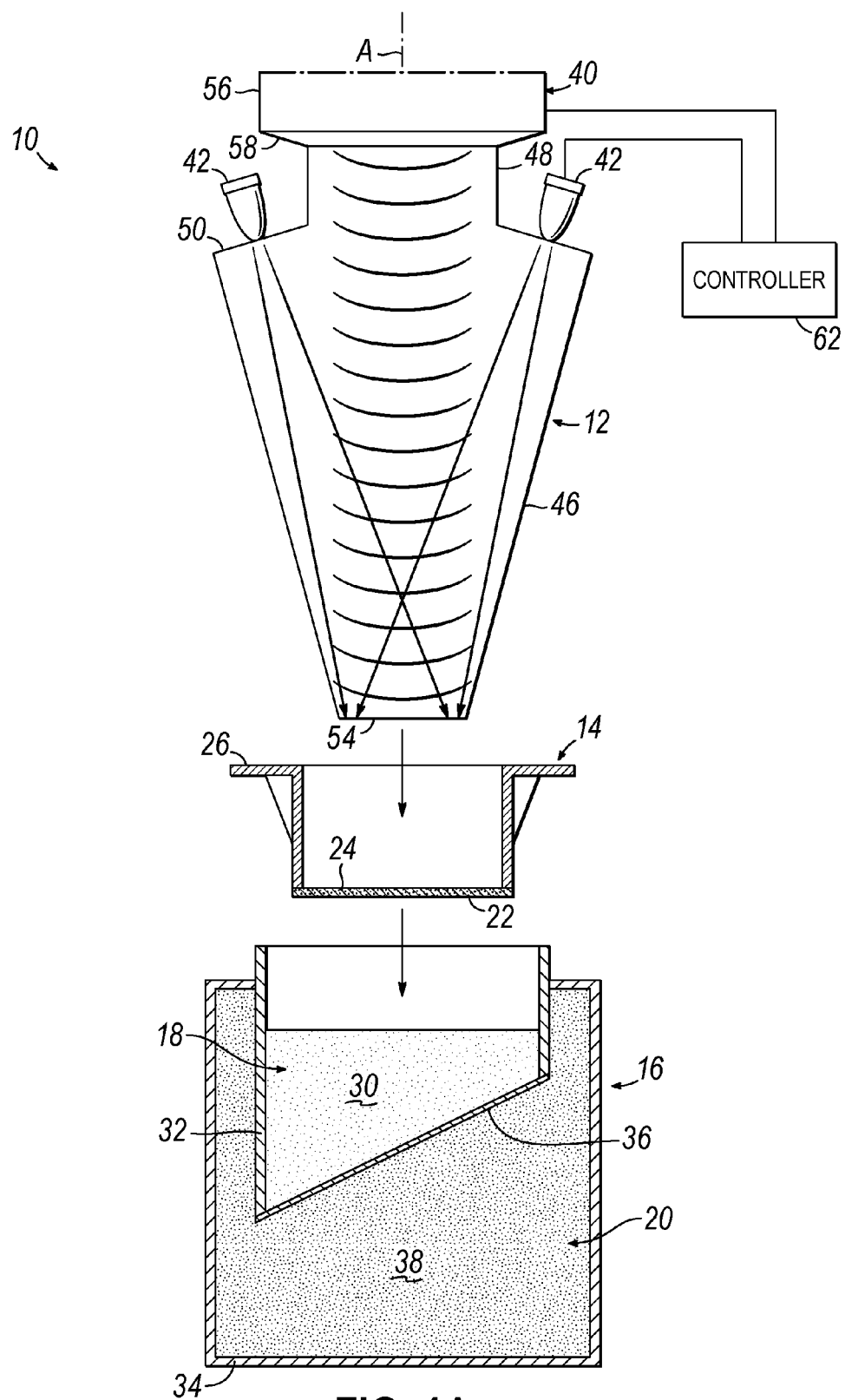
FIG. 1A is a schematic view showing an experimental setup, in a partially disassembled configuration, for treating bacteria with a photo-acoustic treatment device according to an embodiment of the invention.

With reference to FIG. 1A, an experimental setup 10 for treating bacteria with combined ultrasound and light is shown in a partially disassembled configuration. The setup 10 may include a photo-acoustic treatment device 12 according to an embodiment of the invention, a cell culture insert 14, and a container assembly 16 having a treatment chamber 18 and an absorption chamber 20. The setup 10 is described herein in the context of treating a bacterial biofilm. However, the photo-acoustic treatment device 12 may be also be used for treatment of bacteria in a planktonic state using similar or different operating parameters, as described in greater detail below.

Figure 2:
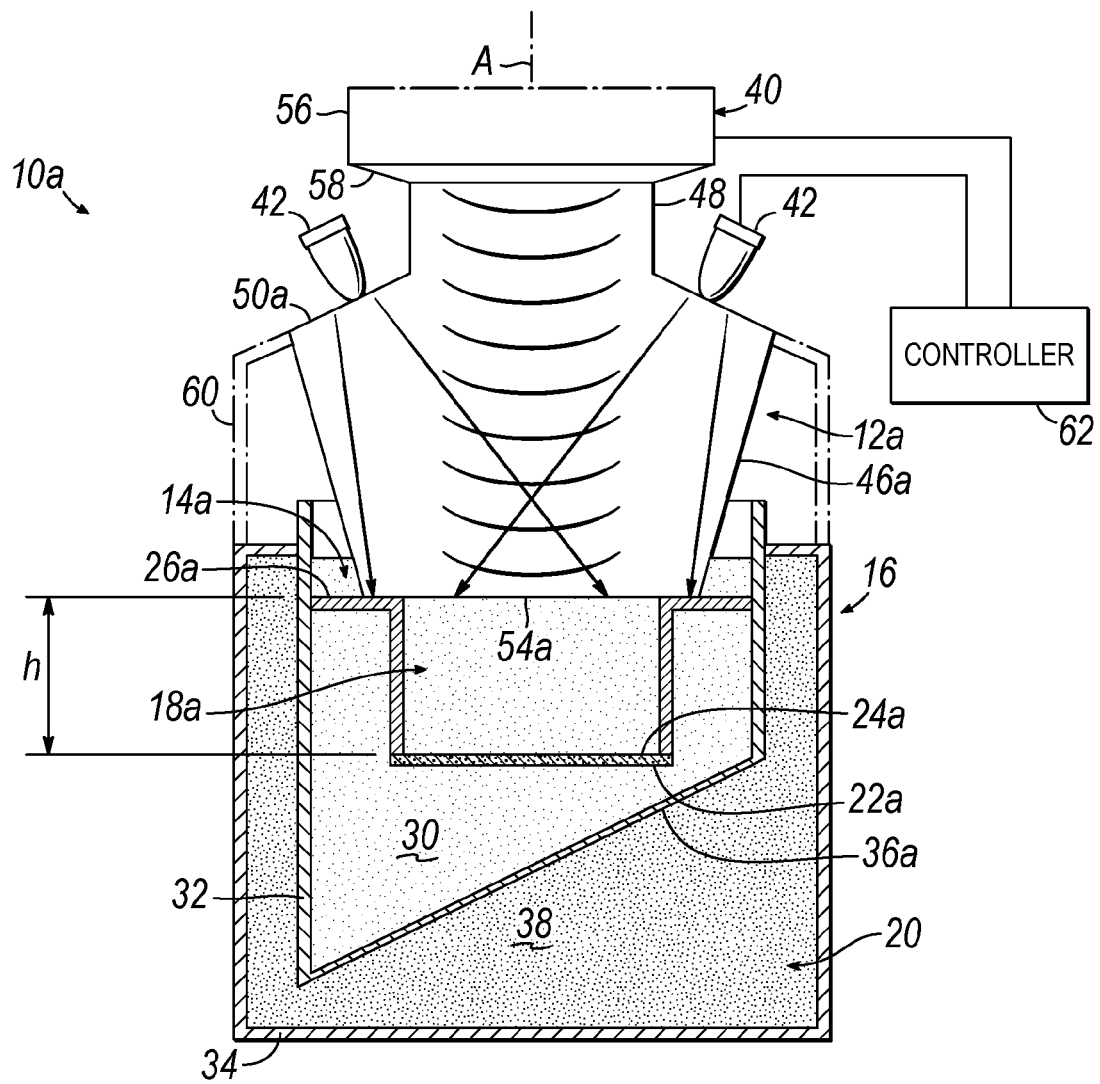
FIG. 2 is a schematic view showing an experimental setup, including a photo-acoustic treatment device, according to another embodiment of the invention.

The cell culture insert 14 may be of any type of structure suitable for growing and harvesting a bacterial biofilm. The insert 14 may include a base surface 22 in the form of a permeable membrane, on which a biofilm 24 may be grown. For example, the base surface 22 may be formed of a thin, permeable layer of polyethylene terephthalate ("PET") of the kind found on a Millicell® hanging cell culture insert. The insert 14 may further include a flange 26 extending radially for supporting the insert 14 within the treatment chamber 18, as shown in FIG. 2.

The treatment chamber 18 of the container assembly 16 is configured to retain an amount of sterile fluid 30, such as phosphate buffered saline ("PBS"), and may be sized such that the base surface 22 of the cell culture insert 14 may be received therein. The treatment chamber 18 is defined by an outer wall 32, which may be in the form of a hollow cylinder extending axially, as shown. A bottom portion of the outer wall 32 may be angularly formed relative to a bottom wall 34 of the absorption chamber 20, which provides advantages described below. The bottom portion of the treatment chamber 18 may be sealed with a fluid-impermeable membrane 36 to prevent fluid exchange between the treatment chamber 18 and the absorption chamber 20. The membrane 36 may be in the form of a thin plastic web, for example.

The absorption chamber 20 of the container assembly 16 is configured to retain an amount of a viscous fluid 38, such as castor oil. The viscous fluid 38 may have a viscosity sufficient to absorb ultrasound energy transmitted to the viscous fluid 38, as described below. As shown, the treatment chamber 18 may extend into the absorption chamber 20 such that the angled bottom portion of the treatment chamber 18 is submersed in the viscous fluid 38 and is suspended above the bottom wall 34. The treatment chamber 18 may be coupled to the absorption chamber 20 with any suitable type of fastening or connection.

The photo-acoustic treatment device 12 may include an ultrasound transducer 40 with an emitting surface, one or more light sources 42, and a photo-acoustic element 46 that is arranged between the combined ultrasound transducer 40 and light sources 42 and the cell culture insert 14. In one embodiment, the photo-acoustic element 46 is generally conical in shape, and includes a cylindrical upper extension 48 extending axially and an annular shoulder 50 defined at the base of the upper extension 48. The annular shoulder 50 may be angled relative to an axis A of the photo-acoustic element 46 as shown, or alternatively the shoulder 50 may be substantially transverse to the axis A. The photo-acoustic element 46 may be a solid structure formed of a translucent, photo-acoustic material configured to transmit light and ultrasound energy simultaneously therethrough and to confine the light and ultrasound energy within its interior with minimal loss and attenuation. For example, the photo-acoustic element 46 may be comprised of thermoplastic or thermosetting polymer, such as an acrylic resin.

The light sources 42 may be in the form of light emitting diodes ("LEDs"), for example UV5TZ-405015 LEDs made available by Bivar, Inc. of Irvine, Calif. While only two light sources 42 are shown, any suitable number of light sources may be used. For example, eight or more light sources may be used, or a single light source may be used. As shown, the light sources 42 may be arranged circumferentially about the upper extension 48 and may be supported by a structure (not shown) that may be mounted to the photo-acoustic element 46 coaxially such that the light sources encircle the upper extension 48 and are positioned adjacent to the annular shoulder 50. The light sources 42 may be positioned angularly relative to the axis A of the photo-acoustic element 46, and are operable to direct light downwardly through the element 46 such that the light reflects through the element 46 and is emitted through an emitting end 54 of the element 46, as indicated by the elongate arrows visible in FIGS. 1A and 1B.

The ultrasound transducer 40 may include a transducer element 56 and a faceplate 58 coupled directly or indirectly to and spanning a width of the transducer element 56. The transducer element 56 may include a piezoelectric ceramic disk, and the faceplate 58 may be formed of any suitable metal such as aluminum, for example. Alternatively, the ultrasound transducer 40 may be constructed as generally shown and described in U.S. Pat. No. 8,206,326, for example, the disclosure of which is hereby incorporated by reference herein in its entirety. In particular, the transducer element 56 may include a plurality of smaller individual transducer elements (not shown herein) embedded in or otherwise surrounded by a polymer matrix material so as to form a piezocomposite structure. Multiple electrodes may be provided on each of the opposed faces of the piezocomposite structure and may be spaced apart so as to permit light to pass through the piezocomposite structure and the electrodes. The electrodes may be elongate bars or concentric rings, for example.

Figure 1B:
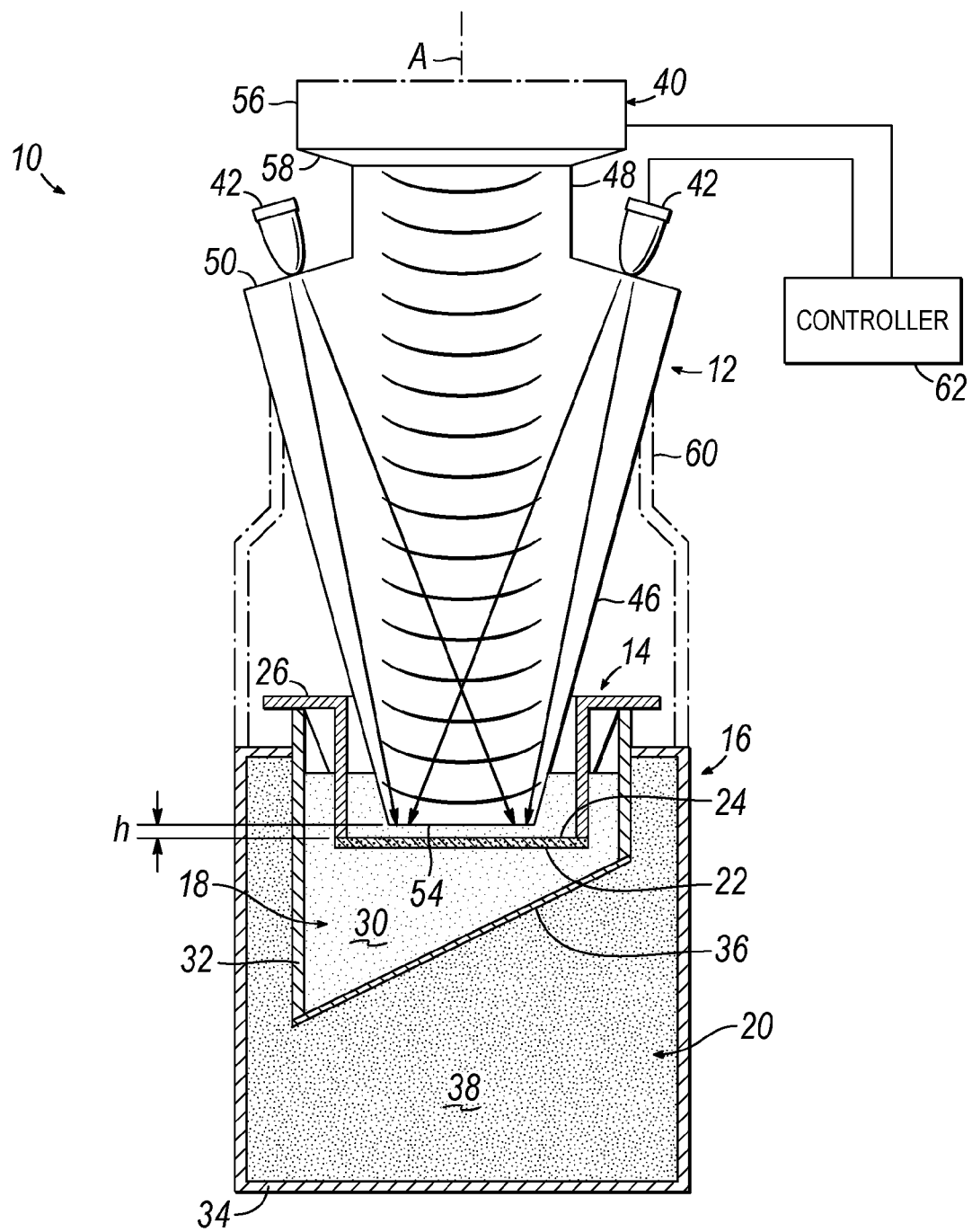
FIG. 1B is a schematic view showing the experimental setup of FIG. 1A in an assembled configuration.

Generally, the transducer element 56 may emit ultrasonic waves when alternating electrical current is applied to its electrodes. The ultrasonic waves may include longitudinal waves, transverse waves, torsional waves, shear waves, surface waves, Raleigh waves, or Lamb waves, for example. As shown in the embodiment of FIGS. 1A and 1B, the transducer 40 may be mounted coaxially with the photo-acoustic element 46 such that the faceplate 58 abuts a top surface of the upper extension 48. In this manner, the faceplate 58 may be acoustically coupled to the photo-acoustic element 46 for transmission of ultrasound energy downwardly through the element 46 and outwardly through the emitting end 54 thereof, as shown generally by arcuate lines visible in FIGS. 1A and 1B.

FIG. 1B shows the experimental setup 10 in an operable configuration, the components thereof being assembled in a manner as indicated by the directional assembly arrows in FIG. 1. As shown, the cell culture insert 14 may be received within the treatment chamber 18 such that the flange 26 is supported by the outer wall 32. Thereby, the permeable base surface 22 of the insert 14 and the bacterial biofilm 24 growing thereon may be suspended within the treatment chamber 18 and submersed in the sterile fluid 30. In this manner, the biofilm 24 may be retained in a sterile environment free of contaminants, including contamination originating from the viscous fluid 38.

A bottom portion of the photo-acoustic treatment device 12 may be received within the cell culture insert 14 and positioned such that the emitting end 54 of the photo-acoustic element 46 is suspended at a fixed height h above the base surface 22 of the cell culture insert 14. Optionally, a support structure 60 of any suitable size or shape may be used to properly align the treatment device 12 relative to the cell culture insert 14 and to suspend the emitting end 54 at the desired fixed height h. In alternative embodiments, the emitting end 54 may be positioned in direct contact with the base surface 22 and the biofilm 24. When the emitting end 54 is spaced from the biofilm 24 as shown in FIG. 1B, the emitting end 54 is submersed in the sterile fluid 30 so that the sterile fluid 30 may form an acoustic coupling with the photo-acoustic element 46. In this manner, the photo-acoustic element 46 is coupled with the biofilm 24 in indirect contact using the sterile fluid 30. The ultrasound energy generated by the transducer 40 may be directed axially through the photo-acoustic element 46, emitted through the emitting end 54, passed through the sterile fluid 30 present in the gap between the emitting end 54 and the base surface 22, and impinge the bacterial biofilm 24. Moreover, the ultrasound transducer 40 may be considered to be coupled to the biofilm 24 in indirect contact established through the photo-acoustic element 46 and the sterile fluid 30.

The base surface 22 of the cell culture insert 14 permits ultrasound energy to be transmitted therethrough. Accordingly, some ultrasound energy may pass through the base surface 22 and continue on through the membrane 36 and into the absorption chamber 20. The viscous fluid 38 in the absorption chamber 20 may operate to absorb such ultrasound energy and thereby alleviate reflection. Furthermore, the angled bottom portion of the treatment chamber 18, and the membrane 36 disposed thereon, may operate to mitigate reflections of ultrasound energy back toward the base surface 22 of the cell culture insert 14. In this manner, the biofilm 24 may be exposed to ultrasound energy that can be well characterized, as the ultrasound only makes a single unidirectional pass through the biofilm.

With reference to FIG. 2, an experimental setup 10a according to another embodiment of the invention is shown. The features of setup 10a are similar to those of setup 10, as indicated by similar reference numerals used in FIG. 2. Additionally, it will be understood that the function of experimental setups 10 and 10a, including photo-acoustic treatment devices 12 and 12a, is substantially similar and that the treatment devices 12, 12a may be used in similar applications. As shown, the photo-acoustic element 46a of treatment device 12a is truncated in length relative to photo-acoustic element 46 of treatment device 12, thereby defining an emitting end 54a having a diameter and cross-sectional area larger than that of emitting end 54. Advantageously, in the context of experimental setup 10a, the emitting end 54a is sufficient in size to span across substantially a full diameter of base surface 22a containing biofilm 24a, thereby enabling the treatment device 12a to provide treatment to a full portion of biofilm 24a. The emitting end 54a may be supported above flange 26a of insert 14a, thereby spacing the emitting end 54a above the base surface 22a by a distance h. It will be understood the components of experimental setup 10a may be modified as desired to space the emitting end 54a at any suitable distance h above, or in direct contact with, base surface 22a. The larger emitting end 54a of treatment device 12a may also prove advantageous in clinical applications for treating a large surface area, such as a back or face of a patient, for example.

The ultrasound transducer 40 of treatment devices 12, 12a may be controlled to generate ultrasound energy using a function generator (not shown) and a power amplifier (not shown). The function generator and power amplifier may be of any suitable types, for example an Agilent 33220A function generator made available by Agilent Technologies of Santa Clara, Calif., and an ENI 325LA power amplifier made available by Electronics & Innovation of Rochester, N.Y. Acoustic energy output by the ultrasound transducer 40 may be measured using any suitable sensor, such as a Reson TC4038 hydrophone made available by Teledyne Reson of Slangerup, Denmark and a model 804 bilaminar membrane hydrophone made available by Acertara Acoustic Laboratories of Longmount, Colo., for example.

The plurality of light sources 42 of treatment devices 12, 12a may be digitally controlled to create light energy using any suitable computer, a USB controlled interface module, and a four-channel pulse-width-modulation ("PWM") light control unit (not shown), for example. The interface module may be a VM116 model made available by Velleman, Inc. of Fort Worth, Tex., and the light control unit may be a CD45 model made available by Digital Lighting Systems of Miami, Fla., for example. Light energy output by the light sources 42 may be measured using any suitable sensor, such as an ILT400 radiometer and a SEL033/W detector made available by International Light Technologies of Peabody, Mass., for example. In one embodiment, the ultrasound transducer 40 and light sources 42 may be controlled by a common controller 62, for example. Alternatively, the transducer 40 and light sources 42 may be controlled by independent controllers.

As described in greater detail below, the treatment devices 12, 12a may be configured to provide combined ultrasound and light energies that overlap spatially (i.e., the emitted energies are spatially coincident). Furthermore, the treatment devices 12, 12a may be controlled to provide the ultrasound and light energies in a continuous mode or in a pulsed mode with complete temporal overlap, partial temporal overlap, or no temporal overlap (e.g., the emitted light and ultrasound may be temporally alternated and interleaved).

The ultrasound energy emitted by the transducer 40 may operate to physically disturb the targeted bacterial biofilm cells. The light energy (e.g., blue light) emitted by the light sources 42 may operate as a bactericide to activate one or more photo-sensitive chemicals within the targeted biofilm cells 24. The photodynamic reaction produces reactive oxygen species, thereby disrupting the cellular structure of the biofilm cells 24 and killing or otherwise deactivating the biofilm cells 24. The bactericidal effect of the light energy is believed to be enhanced by the cellular disturbance imparted by the ultrasound energy that spatially overlaps the light emitted onto the targeted bacteria 24. Thus, whereas ultrasound energy alone or light energy alone may be inadequate to destroy a targeted bacteria effectively, such as a bacterial biofilm 24, the combination of ultrasound energy and light energy according to embodiments of the invention may be sufficient to accomplish an effective and substantial killing, or bactericidal, effect on the bacteria. Further, whereas bacterial biofilms may grow resistant to traditional antibiotic topicals and oral treatments, their structural matrices may be substantially defenseless against spatially overlapping ultrasound and light energies, and furthermore are believed incapable of developing resistance to such combined treatment.

In clinical applications, combined ultrasound and light treatment according to embodiments of the invention may be applied at levels effective to disrupt targeted bacteria cells, such as those of a bacterial biofilm, while remaining safe for use on human tissue. To this end, ranges of various parameters characterizing effective yet safe levels of ultrasound and light energies will now be described according to an embodiment of the invention. The following quantities may be measured at an energy emitting surface of a photo-acoustic device being used (e.g., at emitting end 54, 54a of treatment device 12, 12a), or at any distance from the energy emitting surface representative of an expected location of bacteria to be treated. For example, as described in greater detail below in connection with FIGS. 14 and 16, bacteria being treated may be spaced from the ultrasound emitting portion of the treatment device by layers of intervening tissue and/or other structure. Further, it will be understood that the following energy characteristics may be employed in the use of any of the photo-acoustic treatment devices described herein.

Regarding ultrasound characteristics according to an embodiment of the invention, ultrasound energy may be emitted by the photo-acoustic treatment device 12, 12a at an acoustic output level that may be greater than or equal to 50 kPa and less than or equal to 1 MPa. Acoustic output at levels greater than 1 MPa may undesirably cause destructive cavitations in an aqueous substrate, such as human tissue, on which a targeted bacteria resides. The ultrasound energy may be emitted at a frequency greater than or equal to 20 kHz and less than or equal to 5 MHz. In one embodiment, the frequency may be greater than or equal to 25 kHz and less than or equal to 1.5 MHz. In another embodiment, the frequency may be greater than or equal to 25 kHz and less than or equal to 1 MHz.

Furthermore, the ultrasound transducer 40 may be operated to generate ultrasound at a duty cycle of 5%. For example, during a single repeatable time period, the transducer 40 may be energized for a duration of 0.5 ms and then de-energized for a duration of 9.5 ms. In other embodiments, the transducer 40 may be operated at duty cycles of up to 10%. In this regard, the ultrasound energy may be emitted with a time-averaged sound intensity that may be greater than or equal to 10 mW/cm$^2$ and less than or equal to 1 W/cm$^2$. Accordingly, the photo-acoustic treatment device 12, 12a may emit ultrasound energy with an instantaneous sound intensity that is generally high enough to cause the intended bactericidal effect on the targeted bacteria, and a time-averaged sound intensity that is generally low enough to maintain a safe treatment (i.e., with minimal tissue heating) for use on human tissue covered by the bacteria. The emitted ultrasound may be low energy, and may be focused or non-focused. For example, non-focused ultrasound may be more efficient in applications for treating bacteria covering a large surface area, such as a patient's face or back. Focused ultrasound may be beneficial for targeting a small treatment area and mitigating unwanted treatment of surrounding areas.

Regarding light characteristics according to an embodiment of the invention, light energy may be emitted by the photo-acoustic treatment device 12, 12a with a wavelength in a visible portion of the electromagnetic spectrum that is greater than or equal to 400 nm and less than or equal to 450 nm (i.e., violet/blue). In one embodiment, light energy may be emitted with a wavelength that is greater than or equal to 400 nm and less than or equal to 427 nm. In another embodiment, light energy may be emitted with a wavelength of 405 nm. In another embodiment, light energy may be emitted with a wavelength of 408 nm. In other embodiments, as described below, light energy of longer wavelengths, such as 660 nm for example, may be emitted for treating bacteria.

Persons of ordinary skill in the art will appreciate that light wavelength and light energy are inversely related. To this end, light of wavelength less than 400 nm (i.e., ultraviolet light) may carry energy levels that are hazardous to human tissue. Further, light of wavelength greater than 450 nm carries energy levels that may be inadequate for effectively treating a targeted bacteria, such as a bacterial biofilm, in some applications. The light energy may be emitted from the photo-acoustic treatment device 12, 12a with an averaged light intensity that may be greater than or equal to 5 mW/cm$^2$ and less than or equal to 500 mW/cm$^2$. In one embodiment, the light energy may be emitted with a light intensity of greater than or equal to 30 mW/cm$^2$ and less than or equal to 500 mW/cm$^2$.

Figure 3A:
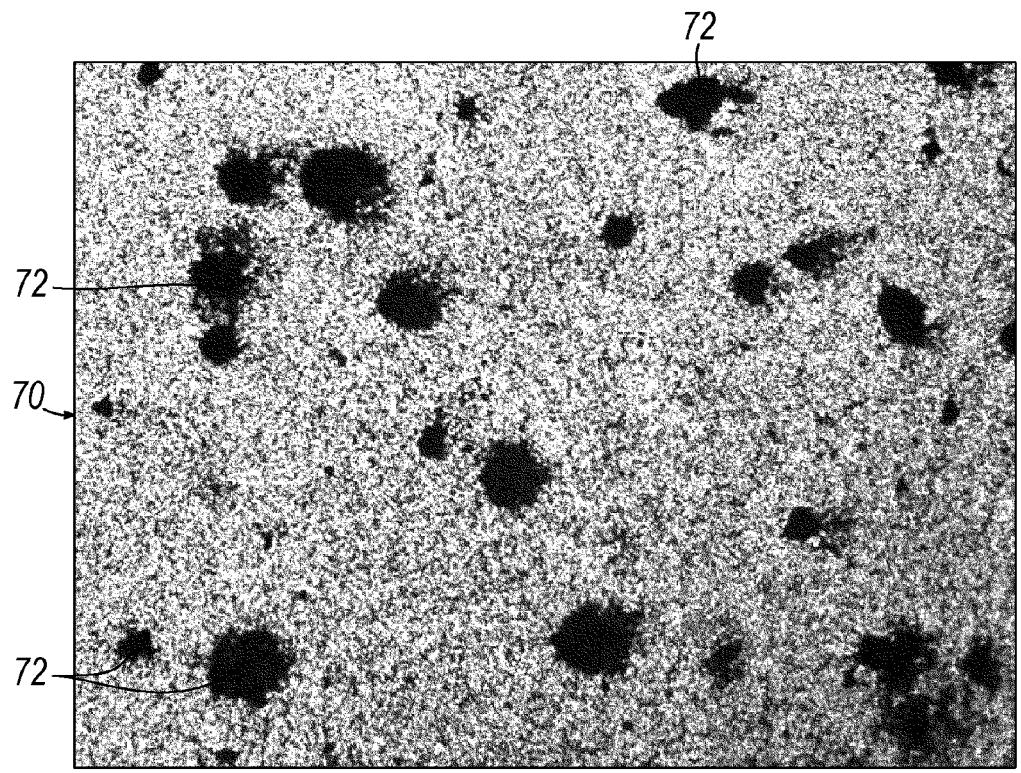
FIG. 3A is a magnified image showing a first bacterial biofilm prior to treatment.
Figure 3B:
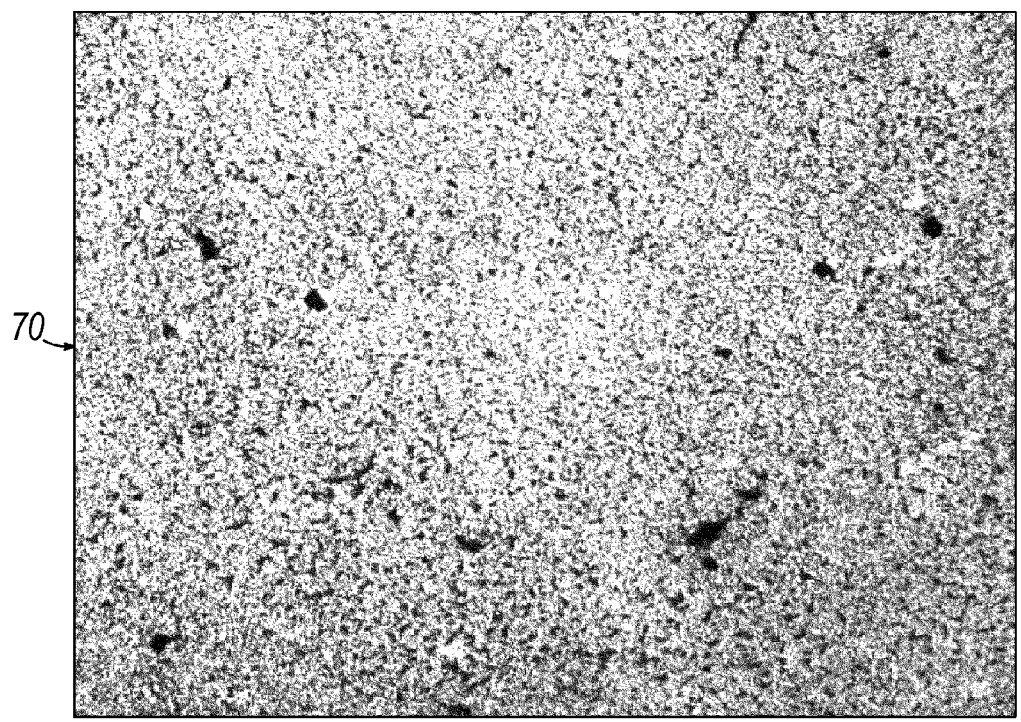
FIG. 3B is a magnified image showing the biofilm of FIG. 3A subsequent to treatment according to an embodiment of the invention.
Figure 3C:
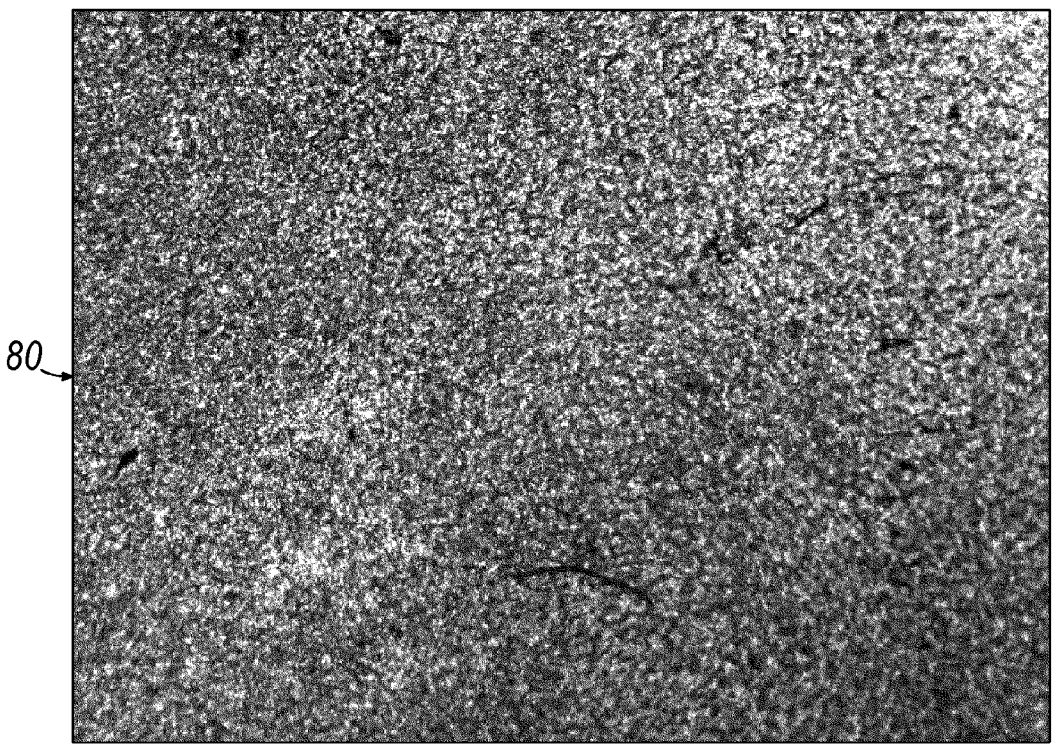
FIG. 3C is a magnified image showing a second bacterial biofilm prior to treatment.
Figure 3D:
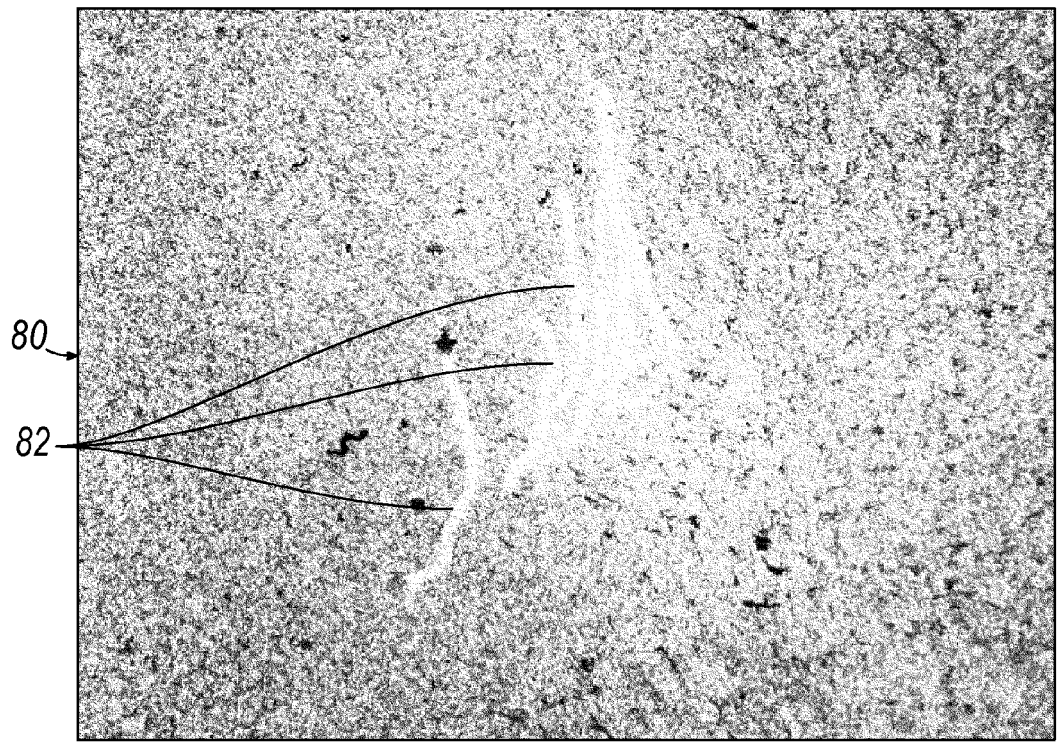
FIG. 3D is a magnified image showing the biofilm of FIG. 3C subsequent to treatment according to an embodiment of the invention.

Turning now to FIGS. 3A-3D, biofilms formed by *Staphylococcus epidermidis* ("Staph. epi." or "*S. epidermidis*"), a commonly occurring bacterium potentially dangerous to humans, are shown before and after receiving combined and simultaneous ultrasound and light treatment according to an embodiment of the invention using photo-acoustic treatment device 12, as described above. The images displayed in FIGS. 3A-3D are shown at approximately 4× magnification. FIG. 3A shows a first *Staph. epi.* biofilm 70 grown on a Tryptic Soy Broth ("TSB") medium that is generally nutrient-rich. The first biofilm 70 was permitted to mature in the nutrient-rich environment for a period of approximately 72 hours, so that visible biofilm colonies 72 could form. FIG. 3C shows a second *Staph. epi.* biofilm 80 grown on a Roswell Park Memorial Institute ("RPMI") medium that is generally nutrient-poor. The second biofilm 80 was permitted to mature in the nutrient-poor environment for a period of approximately 24 hours, and thus visible growths are less evident. The first and second biofilms 70, 80 were each exposed to combined ultrasound and light treatment for a period of approximately 30 minutes, using the experimental setup 10 and under conditions as described above. In this regard, the fixed height h as shown in FIG. 2 was set at approximately 3 mm. After treatment, the cell culture inserts on which the biofilms 70, 80 were grown were flushed with sterile saline and stained using Crystal Violet. However, it will be understood that any suitable stain or dye, such as Crystal Violet, may be used to visually enhance the effects of treatment. Results of the treatments are shown in FIGS. 3B and 3D, respectively.

As shown in FIG. 3B, the visible colonies 72 of the first biofilm 70 were substantially disrupted, and the dead biofilm cells sloughed off after being flushed with saline. As shown in FIG. 3D, disruption of the less-mature second biofilm 80 is evident by crack-like patterns 82 formed in the biofilm 80 after dead biofilm cells were sloughed off after being flushed with saline. Although the experiment described above was performed with the emitting end 54 of the photo-acoustic element 46 positioned at a fixed distance of 3 mm from the surface of the biofilms 70, 80, the emitting end 54 may be positioned at any desired distance from a biofilm or in direct contact with the biofilm, and light and ultrasound emission parameters may be adjusted accordingly.

Figure 4A:
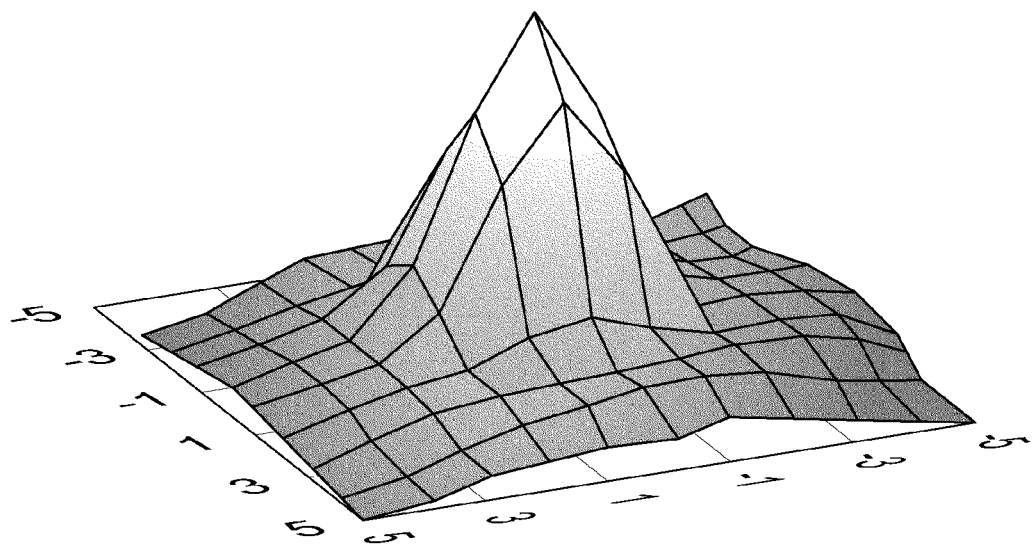
FIG. 4A is a three-dimensional graphical representation on a linear scale of sound intensity data corresponding to ultrasound energy output by a device used for treating bacterial biofilms according to an embodiment of the invention.
Figure 4B:
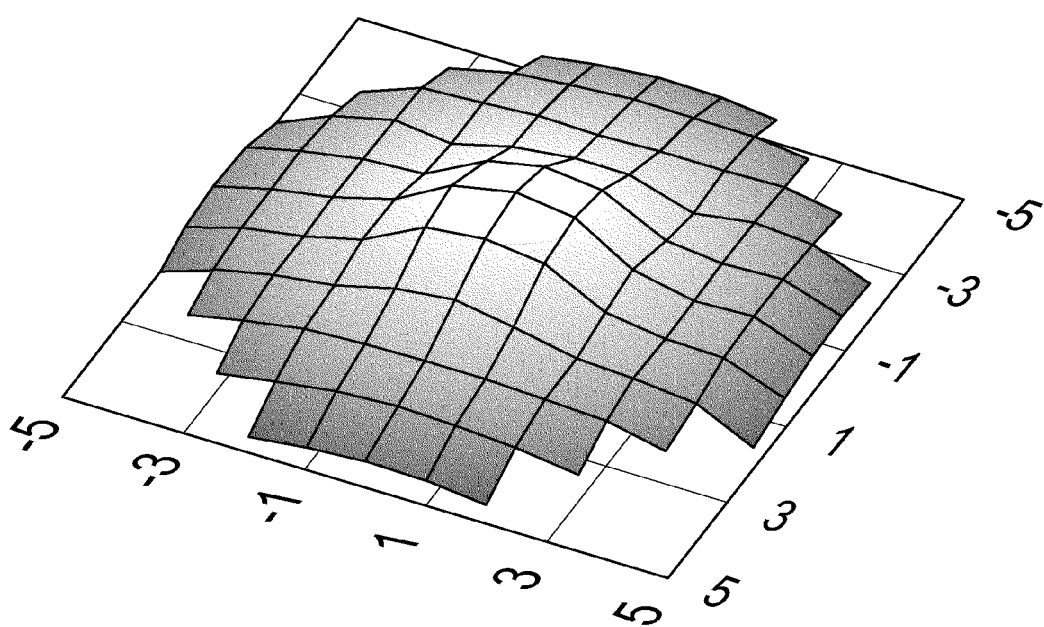
FIG. 4B is a three-dimensional graphical representation of the sound intensity data of FIG. 4A, plotted on a logarithmic scale.
Figure 4C:
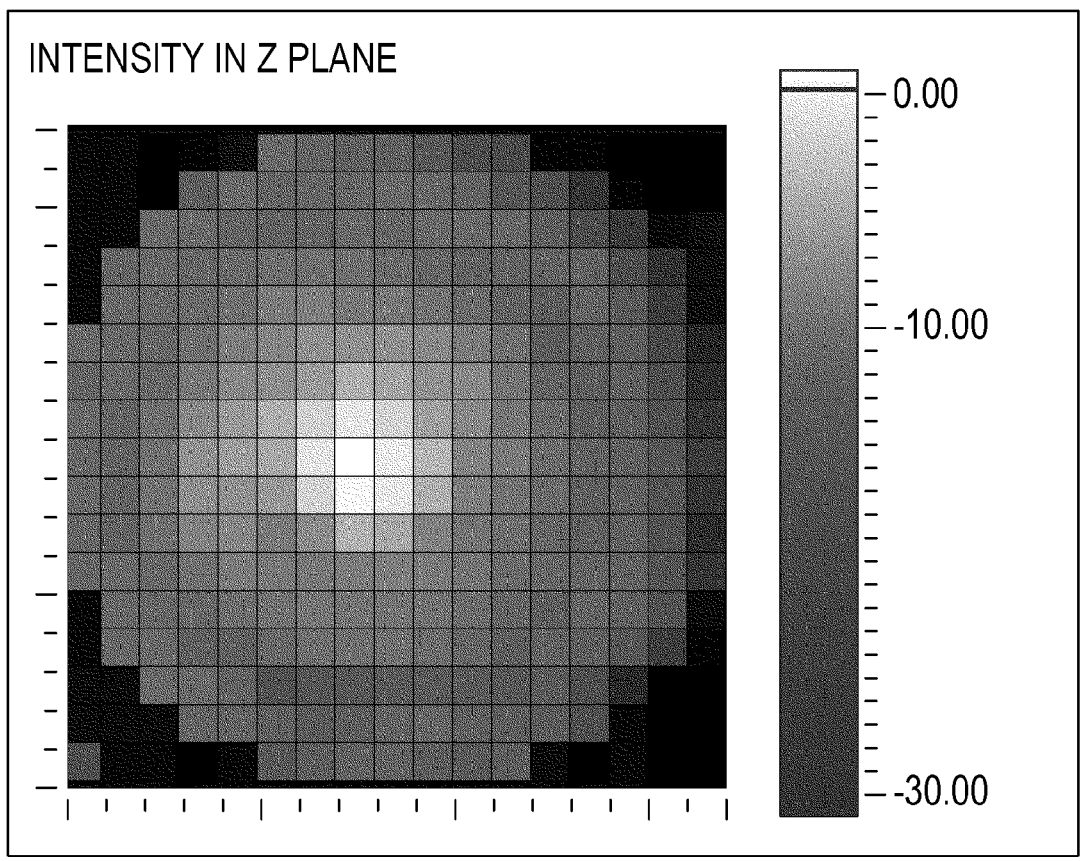
FIG. 4C is a two-dimensional graphical representation of the sound intensity data of FIG. 4A, plotted on a logarithmic scale.

FIGS. 4A-4C show results of acoustic scanning tests performed on the photo-acoustic treatment device 12 to measure and characterize sound intensities similar to those to which the first and second biofilms 70, 80 were exposed during treatment. The plotted sound intensities were measured at an axial distance of approximately 3 mm from the emitting end 54 of the photo-acoustic element 46, i.e., at the approximate location of the first and second biofilms 70, 80 during treatment. Furthermore, the acoustic scanning was performed in a field of 16 mm by 16 mm in a scanning plane substantially parallel to the emitting end 54, with sound intensity measurements being recorded at 1 mm increments along first and second orthogonal axes defining the scanning plane.

FIG. 4A is a three-dimensional graphical representation of the measured sound intensities, plotted on a linear scale. FIG. 4B is a three-dimensional graphical representation of the measured sound intensities, plotted on a logarithmic scale. FIG. 4C is a two-dimensional graphical representation of the measured sound intensities, plotted on a logarithmic scale. The XY origin of the plots shown in FIGS. 4A-4C correspond to the radial center of the emitting end 54 of the photo-acoustic element 46, and the units assigned to the X and Y axes correspond to 1 mm increments in the scanning plane. The Z axes of the plots shown in FIGS. 4A and 4B correspond to the measured sound intensities, as a function of distance from the radial center of the emitting end 54. Similarly, the shading of the plot shown in FIG. 4C corresponds to the measured sound intensities, as a function of distance from the radial center of the emitting end 54. Accordingly, the plots shown in FIGS. 4A-4C each demonstrate that the ultrasound emitted by the photo-acoustic treatment device 12 exhibits the greatest sound intensity, and thus is most effective for disrupting biofilm, at a region of approximately 4 mm by 4 mm at the radial center of the emitting end 54. If it is desired to treat a larger area biofilm, the treatment device (e.g., device 12) may be moved during treatment, or alternatively, redesigned so that a larger effective treatment area results from operation.

Figure 5A:
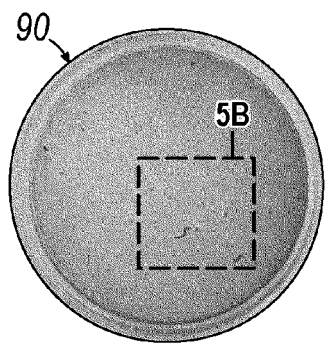
FIG. 5A is an image showing a third bacterial biofilm in an untreated state.
Figure 5B:
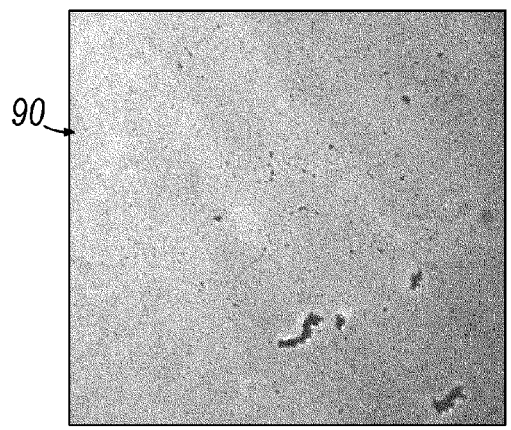
FIG. 5B is a magnified image corresponding to FIG. 5A.
Figure 5C:
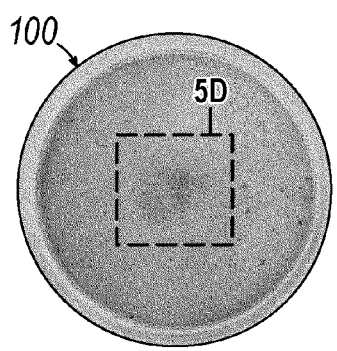
FIG. 5C is an image showing a fourth bacterial biofilm after 30 minutes of treatment according to an embodiment of the invention.
Figure 5D:
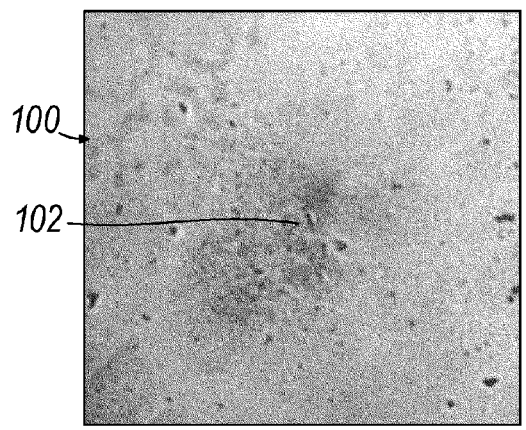
FIG. 5D is a magnified image corresponding to FIG. 5C.
Figure 5E:
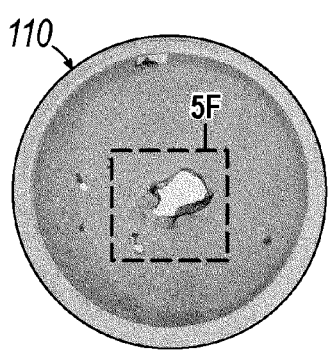
FIG. 5E is an image showing a fifth bacterial biofilm after 60 minutes of treatment according to an embodiment of the invention.
Figure 5F:
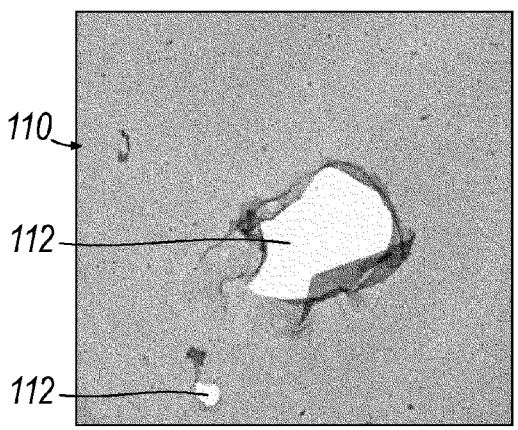
FIG. 5F is a magnified image corresponding to FIG. 5E.

FIG. 5A shows a third *Staph. epi.* biofilm 90 grown in a TSB medium and permitted to mature for a period of 48 hours. FIG. 5B shows a magnified image corresponding to FIG. 5A. FIG. 5C shows a fourth *Staph. epi.* biofilm 100 grown in a TSB medium and permitted to mature for a period of 48 hours, and then treated with combined ultrasound and light for a period of 30 minutes. FIG. 5D shows a magnified image focusing on the zone of treatment of the fourth biofilm 100. As shown in FIGS. 5C and 5D, the fourth biofilm 100 exhibits discoloration and crack-like patterns 102 after treatment, due to dead biofilm cells. FIG. 5E shows a fifth *Staph. epi.* biofilm 110 grown in a TSB medium and permitted to mature for a period of 48 hours, and then treated with combined ultrasound and light for a period of 60 minutes. FIG. 5F shows a magnified image focusing on the zone of treatment of the fifth biofilm 110. As shown in FIGS. 5E and 5F, the fifth biofilm 110 exhibits disruptions 112 after treatment, due to dead biofilm cells that have sloughed off after flushing with saline. The third, fourth, and fifth biofilms 90, 100, 110 were treated using the experimental setup 10 and with ultrasound and light having characteristics as described above.

During testing and in therapeutic treatments, the light profile emitted from the emitting end 54 of the treatment device 12 (or emitting end 54a of treatment device 12a) may at least partially overlap spatially with the acoustical profile at the location of the biofilms 70, 80, 90, 100, 110. The region of spatial overlap between the light energy and the ultrasound energy will provide a synergistic, therapeutic effect resulting in a more effective and substantial disruption of the biofilm, or other bacteria being targeted. Moreover, the light and ultrasound energies may be delivered in a continuous manner or in a pulsed manner with varying degrees of temporal overlap, including complete temporal overlap, partial temporal overlap, or no temporal overlap (e.g., alternating and interleaving light and ultrasound), as described in greater detail below.

Methods of treating biofilms with the combined delivery of light and ultrasound according to embodiments of the invention are shown and described herein primarily with reference to treatment of *Staph. epi.* biofilms. However, parameters of the invention may be adapted for treatment of other bacterial biofilms as well, which are often root causes of many human skin diseases. For example, acne vulgaris and atopic dermatitis are two of the most common childhood diseases and are each caused by presence of bacterial biofilm, and which may be treated using combined ultrasound and light therapy according to the embodiments of the invention. Traditional treatments for these conditions include topical and oral antibiotics and steroids, topical emollients, and calcineurin inhibitors, each of which present safety concerns. Treating such bacterial biofilms, with combined ultrasound and light according to embodiments of the invention may be accomplished through various devices and systems designed for clinical use by physicians and/or for home use by patients. For example, combined ultrasound and light treatment may be delivered with a handheld device, and may be used in combination with various topical gels for ultrasound transmission and various disposable applicator covers to maintain aseptic conditions. Moreover, combined ultrasound and light treatments according to embodiments of the invention are believed to offer additional epidermal benefits. For example, such benefits may include reduced inflammation, induction of skin matrix formation, and facilitation of enhanced healing of lesions. It will be further appreciated that the photo-acoustic treatment devices and methods of treatment using combined mechanical stress and electromagnetic energies shown and described herein may be used in connection with clinical treatments of fungal infections.

Figure 6:
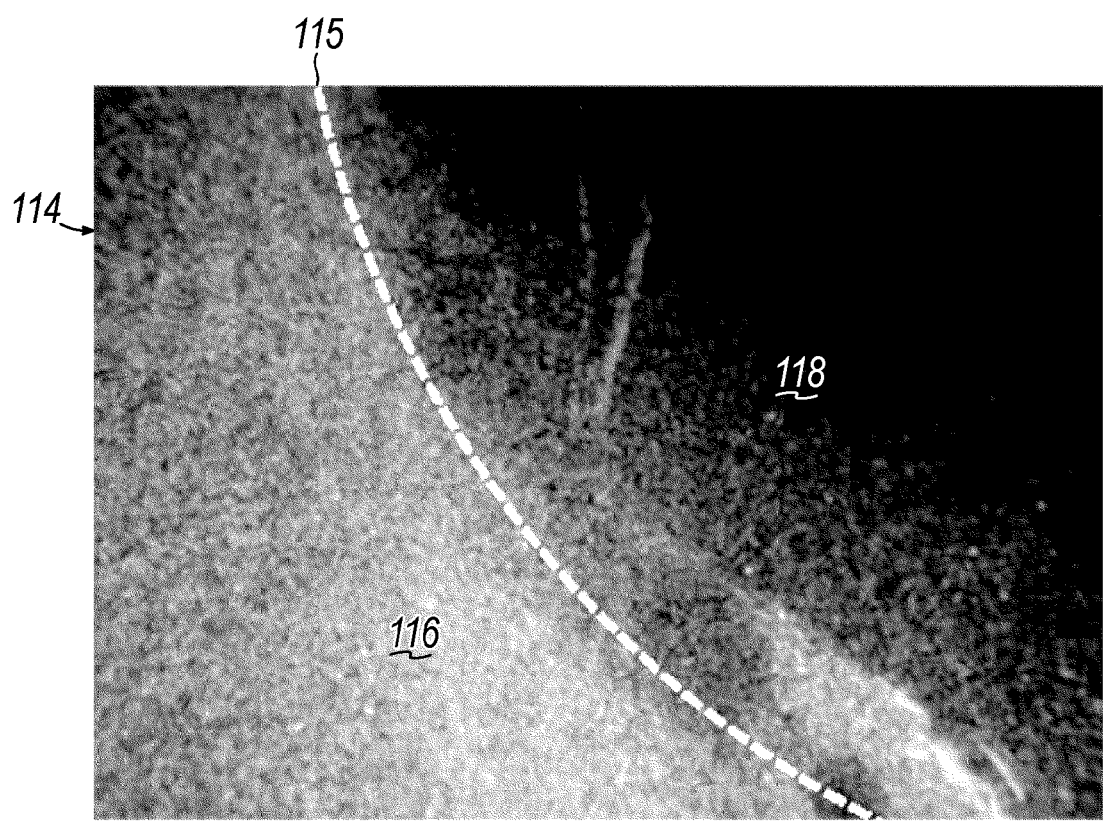
FIG. 6 is an image of a biofilm treated at one region with light only and at another region with combined light and ultrasound according to an embodiment of the invention.

With reference to FIG. 6, an acne bacteria biofilm 114, stained with a dye, is shown after having been exposed to two different types of treatment on either side of diagrammatic line 115. In particular, a first region 116 of the biofilm 114 on the left side of the line 115 was exposed to light alone, and its lighter color indicates a predominant presence of living biofilm cells after treatment. A second region 118 of the biofilm 114 on the right side of the line 115 was exposed to combined ultrasound and light, and its darker color indicates a predominant presence of dead biofilm cells after treatment. Accordingly, the experimental results shown in FIG. 6 demonstrate that combined ultrasound and light treatment is more effective than light treatment alone for damaging and/or killing bacterial biofilm cells.

Figure 7A:
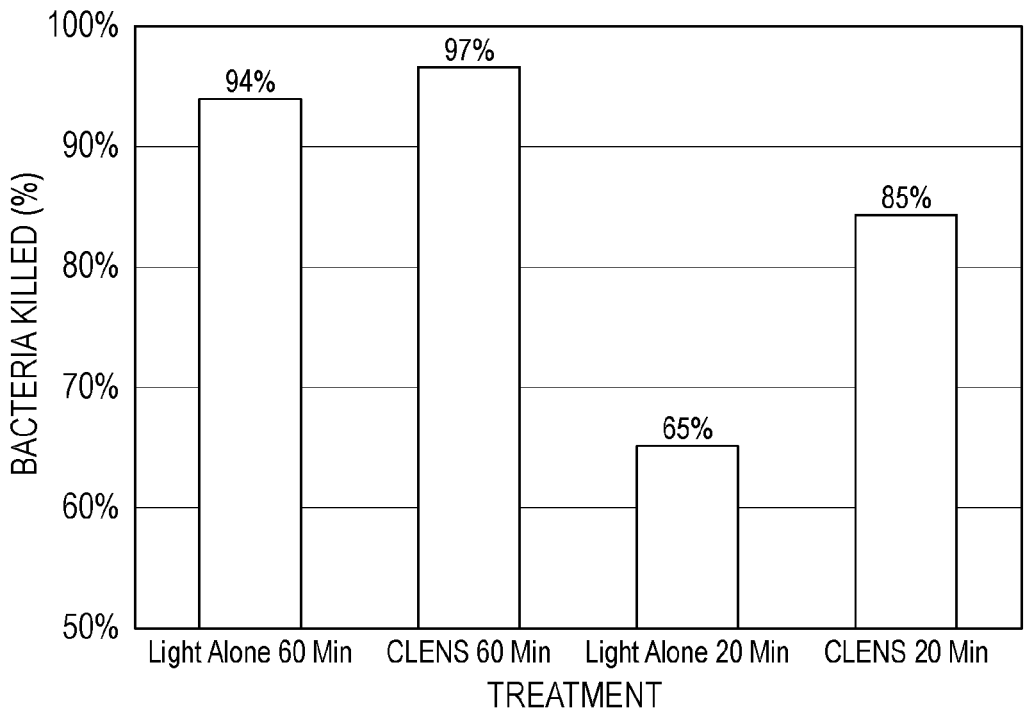
FIG. 7A is a graphical representation of data corresponding to treatment of planktonic bacteria with light alone (e.g., just electromagnetic energy) and with combined light and ultrasound (e.g., electromagnetic energy and mechanical stress energy) according to an embodiment of the invention.
Figure 7B:
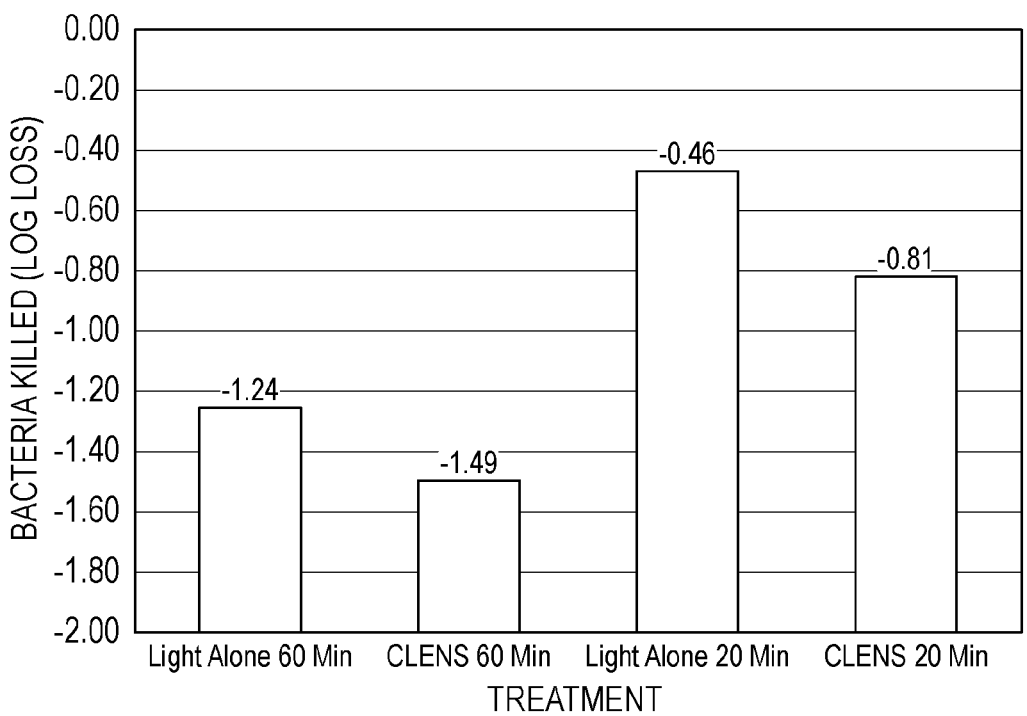
FIG. 7B is a graphical representation of the data of FIG. 7A, plotted according to a logarithmic loss function.

The combined ultrasound and light therapy treatments according to embodiments of the invention may also be used for killing bacteria residing in a free-floating planktonic state or, in other words, a pre-biofilm or non-biofilm state. With reference to FIGS. 7A and 7B, the illustrated bar graphs show experimental data corresponding to treatment of *Propionibacterium acnes* ("*P. acnes*") bacteria grown in a Reinforced Chlamydial Medium (RCM) and matured for three days, at which point the bacteria was in a stationary phase. The bacteria was then suspended in a normal saline solution and treated with either light alone or combined light and non-focused ultrasound energies (CLENS). The light alone treatment was applied with a wavelength of 405 nm (i.e., blue light) and an intensity of 30 mW/cm$^2$. The ultrasound energy was applied at a frequency of 456 kHz, a pressure of 250 kPa, and a 5% duty cycle. After treatment, the bacteria samples were serially diluted and plated on Reinforced Chlamydial Agar (RCA) plates. The RCA plates were incubated at 37 degrees Celsius for seven days under anaerobic conditions and the Colony Forming Units were then counted.

The amounts of planktonic bacteria killed during the experiment as a result of exposure to the two different forms of treatment, which is applied for a period of either 20 minutes or 60 minutes, are shown graphically in FIGS. 7A and 7B. FIG. 7A illustrates experimental results in terms of percentage of bacteria killed. FIG. 7B illustrates the same experimental results shown in FIG. 7A, but plotted according to a logarithmic loss (or "log loss") function. With reference to FIG. 7A, exposure to light alone for a period of 60 minutes killed 94% of the sample bacteria. Exposure to combined light and non-focused ultrasound (CLENS) killed 97% of the sample bacteria. Exposure to light alone for a period of 20 minutes killed 65% of the sample bacteria. Exposure to combined light and non-focused ultrasound for a period of 20 minutes killed 85% of the sample bacteria. The graphed results show that the addition of ultrasound energy produces a significant enhancement of the bactericidal effects of light, particularly during the shorter exposure period of 20 minutes.

Figure 8:
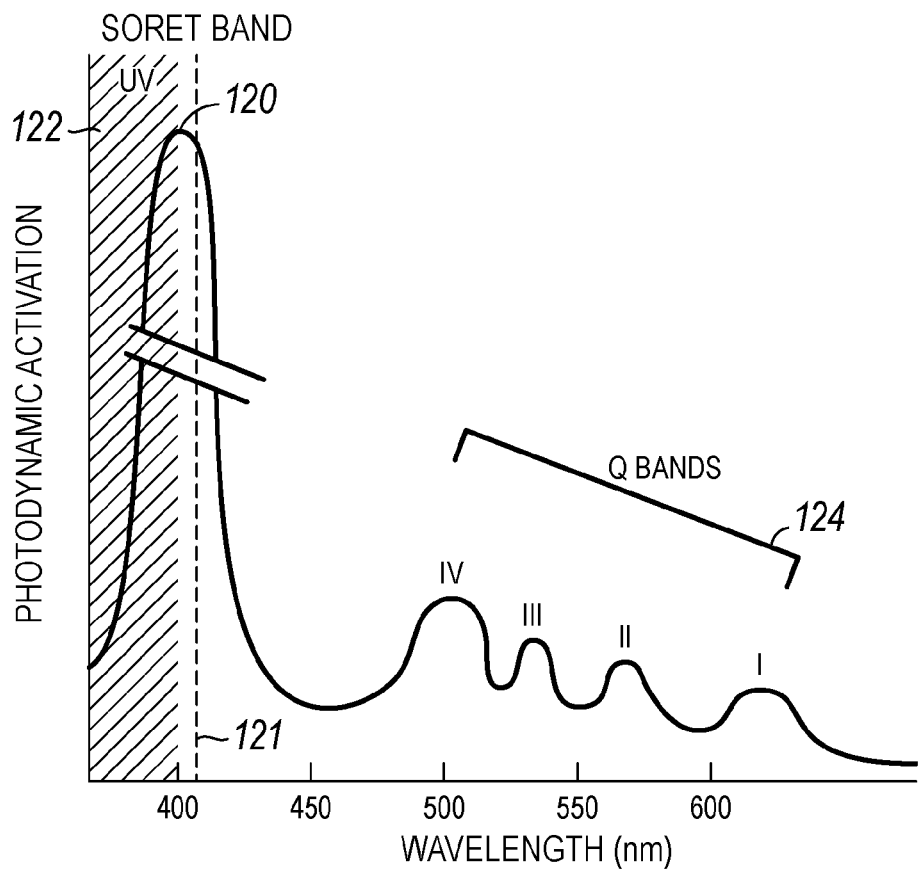
FIG. 8 is a graphical representation of photodynamic activation of chemicals within bacteria as a function of wavelength of light with which the bacteria are treated.

With reference to FIG. 8, the illustrated diagram shows the relative photodynamic activation of chemicals within bacteria as a function of exposure to light of various wavelengths, measured in nanometers. As described above, exposure to light activates specific chemicals within the bacteria, resulting in release of reactive oxygen species, thereby causing bacterial cell disruption and death. Such chemicals may include Protoporphyrin IX (PpIX), which is found in numerous bacteria including *P. acnes, S. epidermidis*, and *Staphylococcus aureus* ("*S. aureus*").

The Soret Band of light, indicated generally at 120 in FIG. 8, is the region of highest photodynamic activity along the visible light spectrum and is centered on the wavelength of 400 nm. The wavelength of 405 nm (i.e., blue light) is indicated in FIG. 8 by a vertically extending dashed line 121, and falls generally within the Soret Band 120 and advantageously outside of the ultraviolet region ("UV") indicated at 122. It will be understood that light in the ultraviolet region has sufficient energy to cause changes in DNA, which can result in skin cancer, and thus may be generally undesirable for use during treatment of human patients. Moreover, as described above in connection with various treatment methods according to embodiments of the invention, light having a wavelength of approximately 405 nm is highly effective for killing bacteria, particularly when the bactericidal effects of the light are enhanced by combined application of ultrasound energy.

Antibacterial effects of light have also been found at wavelengths greater than that of the Soret Band 120, and which thus correspond to lower light energies. For example, longer wavelengths in a region of the electromagnetic spectrum referred to as the Q Bands (e.g., approximately 500 nm to 660 nm), indicated generally at 124 in FIG. 8, have also been found to produce antibacterial effects. While light of longer wavelengths may be less efficient at generating reactive oxygen in a targeted bacteria, light of longer wavelengths may advantageously be subject to less absorption, attenuation, and scattering in tissue than light of shorter wavelengths. Thus, the benefits of longer wavelength light may compensate for its lower energy levels in some applications. Depending upon the application, one skilled in the art may choose from among various light wavelength options, and may combine several different wavelengths in a single treatment device. In one embodiment, light having a wavelength of approximately 660 nm may be used for treatment.

As described above, treating bacteria according to embodiments of the invention using combined light and ultrasound energies may include spatially overlapping the two energies, such that the tissue area being treated is subject to both types of energy. Furthermore, as described in greater detail below, the light and ultrasound energies may be delivered in a continuous manner or in a pulsed manner with complete temporal overlap, partial temporal overlap, or no temporal overlap (e.g., alternating and interleaving light and ultrasound). Moreover, as described above, such combined treatment may be provided with a fully integrated treatment device, such as devices 12, 12a, which may be used for dermatology applications in which the device contacts the skin of the patient to destroy resident bacteria, such as planktonic bacteria and/or bacteria forming a bacterial biofilm. Other applications for killing bacteria may include treatment of wounds, chronic rhinosinusitis, infected catheters, infected implants (e.g., breast implants, hip implants, and other prosthetic joints), endocarditis, chronic middle ear infections, and chronic urinary tract infections, for example.

When treating a surface, for example tissue in medical or cosmetic applications, with combined ultrasound and light, it is often necessary to reach a threshold level of ultrasonic pressure or light amplitude in order to effect an adequate treatment. Such ultrasound pressures may be approximately 100 kPa, 200 kPa, or 500 kPa, for example, and such light intensities may be approximately 30 mW/cm², 50 mW/cm², or 100 mW/cm², for example. If the ultrasound energy is delivered in a continuous manner (i.e. with a continuous, uninterrupted amplitude, as defined by international standards and as known in the engineering arts), then the total power delivered may be sufficiently high to cause a temperature rise and potentially cause tissue damage. Therefore, it may be advantageous to deliver ultrasound energy in a pulsed mode, in which a first higher amplitude burst of ultrasound energy of a finite duration is followed by a second lower amplitude (or zero amplitude) burst of energy of an equal, smaller, or longer duration. This pattern may be repeated for the full extent of the treatment period. Advantageously, by pulsing ultrasound energy, it is possible to deliver instances of higher pressure amplitude while maintaining the same overall power level at a continuous application of lower pressure. In various embodiments, light energy may be pulsed in a similar manner.

With reference to FIGS. 9-12, several embodiments of continuous and pulsed energy application are shown graphically. It will be understood that continuous or pulsed energy application, or combinations thereof, may be employed in connection with the delivery of ultrasound and light energies by any one of the photo-acoustic treatment devices 12, 12a, 130, 150, 170, and 220 described herein, the latter of these devices being described in detail below.

Figure 9:
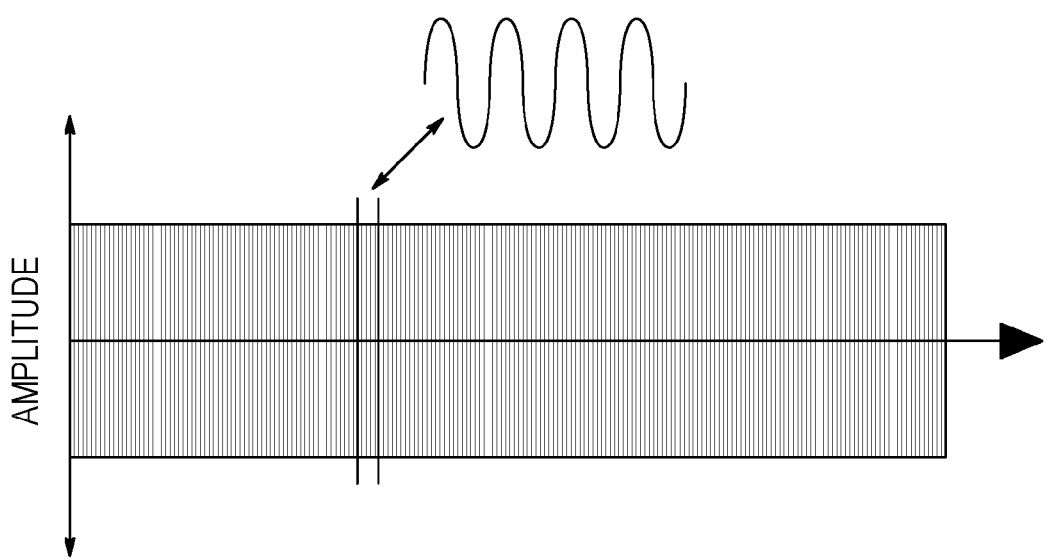
FIG. 9 is a graphical representation of a continuous waveform of energy emitted for treating bacteria according to an embodiment of the invention.

As shown in the graph of FIG. 9, ultrasound and/or light may be delivered as a continuous wave of energy, referred to as Continuous Wave (CW) or Continuous Mode treatment. With Continuous Wave treatment, there is no temporal interruption of the energy deposition throughout the duration of the treatment. The "Amplitude" denoted by the vertical axis of the graph in FIG. 9 may refer to the amplitude of an ultrasonic pressure wave or the amplitude of light, for example. The horizontal axis represents progression of time during a period that an energy emitting element (e.g., an ultrasound transducer or a light source) is energized to emit energy for treatment, and during which period the emitted wave of energy may continuously rise and fall in a sinusoidal manner, as indicated by the magnified portion of the graphed wave. As described above, Continuous Wave application of ultrasound energy may undesirably prove destructive to host tissue at some high energy or power levels, and thus, pulsed application of energy may be preferred in some applications, as described below.

Figure 10:
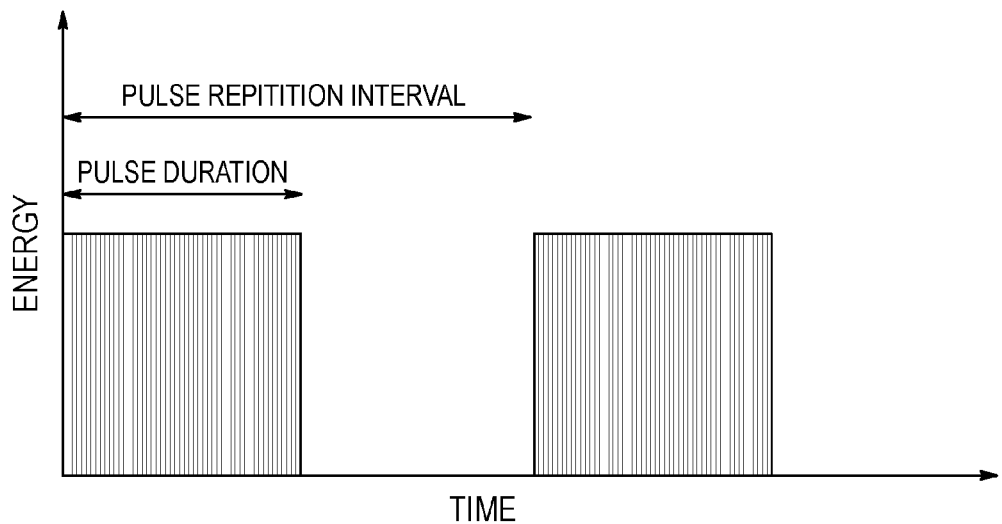
FIG. 10 is a simplified graphical representation of a pulsed waveform of energy emitted for treating bacteria according to an embodiment of the invention.

In another embodiment of treatment, ultrasound energy and/or light energy directed at bacteria, for example with one of photo-acoustic treatment devices 12, 12a, 130, 150, 170, or 220 described herein, may be delivered in a pulsed mode for a full or partial portion of a treatment period. With reference to FIG. 10, a pulsed waveform of an energy (e.g., light or ultrasound) is shown in simplified form. It will be understood that the pulsed waveform may be of a sinusoidal or similar shape, comprising both positive and negative energy valves (e.g. pressure of a sound waveform, or amplitude of a light waveform). As shown, the time period during which the energy is turned "on" (i.e., emitted) is referred to as a Pulse Duration (PD), or Pulse Length. The time period over which the pulse repeats is referred to as the Pulse Repetition Interval (PRI). The reciprocal of the Pulse Repetition Interval is referred to as the Pulse Repetition Frequency (PRF). The Duty Cycle (DC), or Duty Factor (DF), is a ratio of the Pulse Duration to the Pulse Repetition Interval (PD/PRI), and indicates the percentage of a given time period that the energy is on. As such, a Duty Cycle of 100%, in which the Pulse Duration is equal to the Pulse Repetition Interval, indicates Continuous Wave operation. The Duty Cycle also represents the percentage of the maximum possible energy delivery for a given wave amplitude.

When delivering both ultrasound and light to a target, whether biological (e.g. tissue) or non-biological (e.g. a ship hull, medical catheter, or other structure coated with biological material), the two energies may be spatially coincident, meaning that both energies may be directed to the same location in space. In other words, the beams of energy may overlap spatially. As described above, due to the nature of the ultrasound energy and light energy delivery processes and the potential positive and/or negative reactions of biological materials to these energies impinging upon biological materials, it may be advantageous to deliver the combined energies (e.g., one or both of the ultrasound energy and the light energy) in a pulsed mode rather than a continuous mode. Further, it may be advantageous to deliver the pulsed ultrasound and/or light energies with varying degrees of temporal overlap, including full temporal overlap, partial temporal overlap, or no temporal overlap, for example.

There are several reasons why one skilled in the art would choose to deliver the ultrasound and light energies in a pulsed manner rather than a continuous manner. As described above, it may be necessary to generate a certain level of pressure or light energy in order to effect an adequate treatment in a given application. The attenuation of both sound and light through tissue generally limits the depth of penetration of each type of energy. By increasing the amplitude of an energy, the energy can reach a greater depth. Increased amplitude in Continuous Wave application may cause unwanted heating and degradation of the energy emitting instrument (e.g., a piezoceramic transducer or LED light source) or unwanted heating and degradation of the targeted tissue, as described above. By pulsing the emitted energy, the average energy level may be maintained at a safe degree while the peak energy may be increased to effect the desired treatment.

An additional reason for using ultrasound in a pulsed mode relates to the issue of standing waves. When ultrasound travels from a first medium to a second medium having a different acoustic impedance than the first medium (e.g., from tissue to bone, water to plastic, or water to steel), some amount of the ultrasound energy may be reflected back towards the ultrasound transmitter. This reflected energy may interact with the transmitted energy to create regions of higher and lower pressure amplitude which are fixed in space, and which are known as standing wave patterns. Standing wave patterns can be especially problematic when treating patients. For example, standing waves may give rise to undesirable excess heat generation within the tissue. Using ultrasound in a pulsed mode reduces the likelihood of such excess heat generation.

Figure 11:
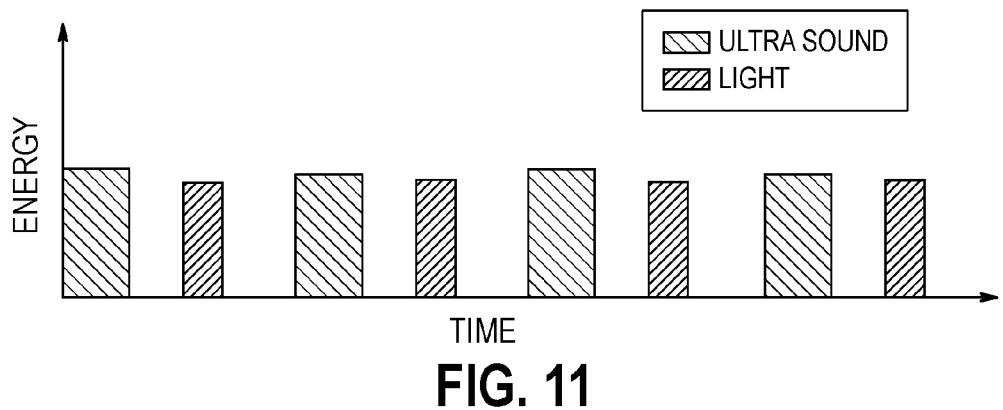
FIG. 11 is a simplified graphical representation of pulsed ultrasound and light emitted in a temporally alternating and interleaved manner for treating bacteria according to an embodiment of the invention.

FIG. 11 shows an exemplary treatment with pulsed ultrasound and light in which there is no temporal overlap of the two energies, such that the delivery of the two energies is alternating and interleaved. Additionally, as shown, the Pulse Repetition Interval for each energy may be the same, and the two energies may be effectively synchronized. Of course, in alternative embodiments the Pulse Repetition Interval may not be the same for both energies, leading to some overlapped pulses and other non-overlapped pulses.

A beneficial result of delivering the pulsed ultrasound and light energies with no temporal overlap, such that the energies are alternated and interleaved as shown in FIG. 11, is maintaining a balanced energy load on the energy generation equipment. In this regard, a power supply may be limited in operation to a particular average power consumption. When the emitted energy pulses are overlapped temporally, they create a combined power consumption that is higher than an individual power consumption corresponding to either one of the energies, and which combined power consumption might undesirably extend beyond the operational limits of a particular power supply.

Figure 12:
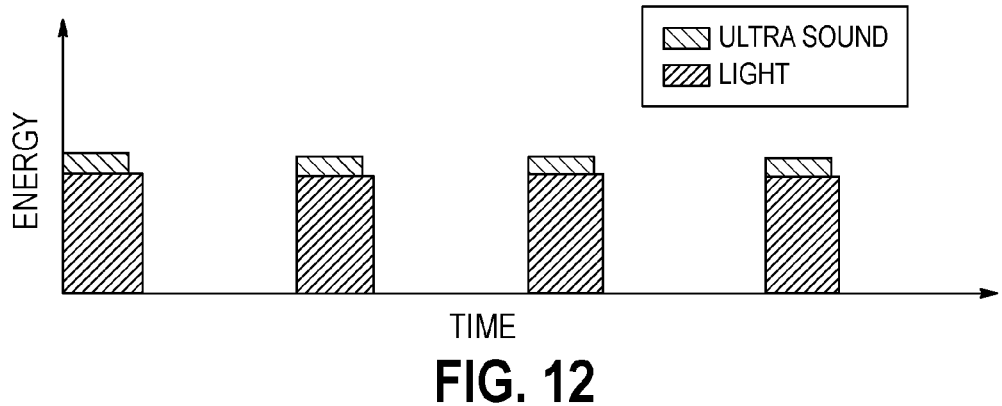
FIG. 12 is a simplified graphical representation of pulsed ultrasound and light emitted in a temporally overlapping manner for treating bacteria according to an embodiment of the invention.

FIG. 12 shows another exemplary treatment with pulsed ultrasound and light in which the two energies fully overlap temporally during a portion of the overall Pulse Repetition Interval, each of the energies having the same Pulse Repetition Rate. As shown in FIGS. 11 and 12, the Pulse Duration of the light energy may be greater than or less than (and in other embodiments, equal to) the Pulse Duration of the ultrasound energy, so as to deliver the light energy with a Duty Cycle greater than or less than (and in other embodiments, equal to) a Duty Cycle of the ultrasound energy. Additionally, where the ultrasound and light energies fully overlap temporally, they may be synchronized such that the respective pulse of each energy starts at the same time.

Additionally, with respect to a light source (e.g., an LED) of a photo-acoustic treatment device, a maximum amplitude of the light may be set by controlling the maximum current through the light source. The average light output may be set by adjusting the Duty Factor. Any suitable controller may be used for performing these functions, such as a CD400-DMX controller made available by Digital Lighting Systems, for example. The controller may operate with a fixed Pulse Repetition Frequency of 100 Hz (PRI of 10 milliseconds), and a Duty Factor which may be adjusted digitally over a range of 0 to 255, which corresponds to a Duty Factor of 0% to 100%, for example.

In one embodiment, and in the interest of mitigating financial burdens on a user, it may be desirable to drive each of the ultrasound and light energy sources with independent power sources, such that there is no synchronization between the two energy sources. For example, the ultrasound source may have a higher or lower Pulse Repetition Frequency than that of the light source, in which case there would be no synchronization between the two energy sources. Depending upon the exact Duty Factor of each energy, the percentage of overlap of the light and ultrasound energies could vary from near zero to near 100%, and could change as a function of time, for example.

Through experimentation, it has been discovered that a range of Pulse Durations and Pulse Repetition Intervals may be effective for killing bacterial biofilms. Exemplary experiments were conducted on *P. acnes*, *S. epidermidis*, and *S. aureus*. Operating parameters which have proven effective, through experimentation, for treating bacteria biofilms include Pulse Repetition Intervals of 1 ms to 100 ms (i.e., Pulse Repetition Frequencies of 10 Hz to 1000 Hz), Pulse Durations of 100 microseconds to 2 milliseconds, ultrasound Duty Factors of 1.1% to 11%, and light Duty Factors of 2% to 100% (i.e., continuous light exposure in some cases). It has been found that separate exposures of ultrasound only and then light only, or the reverse, are not as effective for killing bacteria. The ultrasound effect on bacteria, which, for instance, may enhance the susceptibility of the bacteria to treatment by light, is relatively short lived (e.g., only a few seconds). Accordingly, in one embodiment, any spatially coincident ultrasound and light treatment may be applied to the bacteria within less than approximately one second of each another. For example, the ultrasound energy delivery may be repeated at least once every other second. In this manner, a cumulative dose of energies may be delivered to the bacteria, because there is not enough time between pulses for the collective and/or combined bactericidal effect of the energies to diminish.

Accordingly, a pulsed mode of energy exposure may be as effective as a Continuous Wave mode of energy exposure, but with potentially higher peak amplitudes for effecting enhanced treatment. In this regard, a targeted bacteria (e.g., on a tissue) does not respond quickly enough to sense a difference between continuous excitation and rapidly pulsing excitation (e.g., at 10 times per second or greater). Additionally, where the mechanism of action of ultrasound is through the force that is applied to the bacteria through acoustic radiation force (e.g., mechanical stress forces), energy pulsations may have a greater effect on the bacteria than continuous excitation, which produces a constant force on the bacteria. In that regard, bacteria cells may adapt to constant forces, and thus the effect provided by a constant force may diminish quickly with time. By pulsing the energies, the bacteria cannot adapt to the changing conditions, and the advantageous combined effect of the energies may continue throughout the treatment time.

Figures 13, 14:
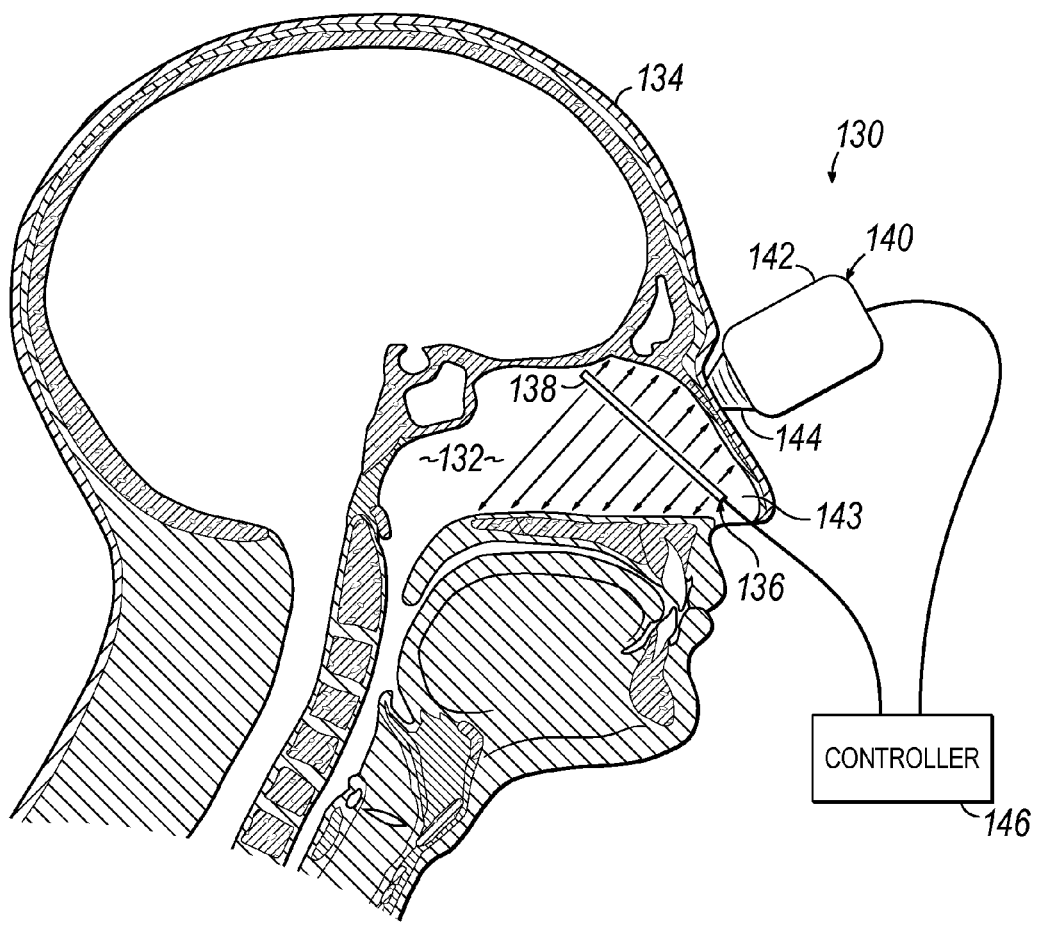
FIG. 13 is a table showing experimental parameters and results corresponding to a treatment of bacteria with combined ultrasound and light energies according to an embodiment of the invention.
FIG. 14 is a schematic view of a photo-acoustic treatment device according to another embodiment of the invention.

During another exemplary experiment, the results of which are summarized in FIG. 13, subjects were exposed to combined ultrasound and light using treatment device 12a held in direct contact, at emitting end 54a, with the skin of each subject at the emitting end 54a, which was formed with a diameter of approximately 29 mm. In this manner, bacteria residing on the skin at levels beneath the outermost surface of the skin (e.g., at 0.1 to 0.9 mm beneath the outermost surface of the skin, for example) were coupled to the photo-acoustic element 46a in indirect contact established through intervening (e.g., overlying) layers of skin. In that regard, it will be understood that coupling via indirect contact between bacteria and a photo-acoustic treatment device treating the bacteria may be established through one or more layers of overlying bodily tissue (e.g., skin) positioned between the bacteria and an energy emitting surface of the treatment device. Further, as described above and below, coupling via indirect contact between bacteria and a photo-acoustic treatment device may be established through an acoustic coupling medium, such as an acoustic coupling liquid, positioned between the bacteria and an energy emitting surface of the treatment device. Accordingly, contact is always provided between the bacteria and the photo-acoustic treatment device, even when a "direct contact" with the bacteria is rendered impossible by the test setup or by the physical location of bacteria on the body.

The treatment device 12a was controlled to provide an ultrasound Pulse Repetition Frequency of 200 Hz and an ultrasound pulse duration of 275 microseconds, or a Pulse Repetition Frequency of 100 Hz and a pulse duration of 550 microseconds. Both combinations produced the same intensity and power levels. The treatment device was further controlled to provide a light Pulse Repetition Frequency of 100 Hz and a light Duty Cycle of 95%. The subjects were exposed to the combined pulsed ultrasound and light for periods varying between 20 minutes and 60 minutes. Skin swabs were then taken and the collected bacteria was cultured for 7 days in growth medium. The resultant Colony Forming Units of *P. acnes* bacteria were then counted. On each subject, two regions were sampled: one region which had been treated, and another untreated control region nearby (e.g., an untreated control region at a contralateral position on a subject's face). The aforementioned step provided a measure of the nature variation in bacterial levels for each subject. Differences between the sample taken before the treatment and 24 hours after the treatment were noted, with corrections made based on the untreated control regions. The above-described operating parameters and corresponding experimental results for each patient are summarized in the table shown in FIG. 13. As shown in the experimental results summary of FIG. 13, the bacterial reduction rates ranged in all but one subject from 72% to 98% with combined, pulsed light and ultrasound energies. The sample plates used for test subject 4 appeared to contain other types of bacteria beyond *P. acnes*, which negatively affected the results. Although not shown in the table of FIG. 13, exposure to light alone produced an average bacterial reduction of 25%, and exposure to ultrasound alone produced no measurable bacterial reductions. These results indicate that a pulsed, spatially overlapping application of combined light and ultrasound energies provides an effective and substantial treatment for killing bacteria.

In various applications using combined ultrasound and light treatment in accordance with the principles of the invention described above, it may be desirable to separate the ultrasound emitting portion from the light emitting portion, or otherwise reconfigure the positioning of these two energy emitting components relative to each other such that the two energies may be emitted from separate device surfaces (i.e., in contrast to treatment devices 12, 12a in which the two energies are emitted from a common device surface 54, 54a). Exemplary embodiments of such alternative photo-acoustic treatment devices are described in greater detail below in connection with FIGS. 14-16. In using treatment devices of such embodiments, a light emitting portion may be directed at bacteria while a separate ultrasound emitting portion may be independently directed at the same bacteria. In this manner, a light profile emitted by the light emitting portion and an acoustic profile emitted by the separate ultrasound emitting portion may overlap spatially at a targeted region of the bacteria to thereby disrupt the targeted bacteria. Separate light and ultrasound emitting portions may be particularly useful when the bacteria to be treated is disposed on a surface that is not easily accessed with an integrated treatment device, such as treatment devices 12, 12a.

With reference to FIG. 14, a photo-acoustic treatment device 130 according to another exemplary embodiment is shown for treating bacteria, such as sinusitis affecting internal bodily surfaces of a sinus cavity 132 of a patient 134. The treatment device 130 may include a catheter-like light emitting portion 136 having a generally cylindrically shaped light emitting probe 138, and a separately formed ultrasound emitting portion 140 having an ultrasound transducer 142, which may be similar in construction to transducer 40 described above. As shown, the light emitting probe 138 may be inserted through a nasal cavity 143 of a patient and guided into the sinus cavity 132 to direct light directly onto the infected surfaces of the sinus cavity 132. Moreover, the light emitting probe 138 may emit light from a complete or partial portion of its outer circumference. For example, the light emitting probe 138 may emit light uniformly from a full 360 degrees of its outer circumference, or from less than 360 degrees of its outer circumference, depending on the requirements of the treatment application.

As shown in FIG. 14, the ultrasound transducer 142 may be positioned extracorporeally in acoustically coupling engagement with external facial tissue overlying the infected inner surfaces of the sinus cavity 132 to be treated. For example, the ultrasound transducer 142 may be placed in direct contact with the facial tissue or may be coupled with the facial tissue in indirect contact via an acoustic coupling medium 144, which may be an intermediate solid structure or an acoustic coupling fluid, for example. Accordingly, ultrasound energy may be transmitted inwardly through the facial tissues toward the infected inner surfaces of the sinus cavity 132. In this manner, the ultrasound transducer 142 may be considered to be coupled to the infected inner surfaces in indirect contact established through the facial tissues and the acoustic coupling medium 144. The light emitting portion 136 and the ultrasound emitting portion 140 may be coupled to a common controller 146, which may control the light emitting probe 138 and the ultrasound transducer 142 to deliver the light and ultrasound energies in a spatially coincident manner such that their energy distribution patterns at least partially overlap in space on the infected surfaces of the sinus cavity 132 being treated. In another embodiment, the light emitting portion 136 may be combined with an additional device (not shown) for performing a sinuplasty to breakup and disrupt the sinus infection.

The photo-acoustic treatment device 130, or a treatment device having a substantially similar configuration, may be used for treating other internal bodily surfaces having bacterial infections as well. In such treatment applications, the ultrasound transducer 142 may be positioned extracorporeally, in coupling engagement with external skin overlying the infected internal surfaces, and the light emitting probe 138 may be inserted through a body orifice or other body opening and positioned proximate the infected internal surfaces. The ultrasound transducer 142 may be operated to transmit mechanical stress energy through the overlying skin and internal bodily tissues toward the infected surfaces, while the light emitting probe 138 may be operated to emit electromagnetic energy directly onto the infected surfaces. In this manner, the emitted energies may overlap spatially on the infected surfaces to thereby disrupt the bacteria causing the internal infections. Additionally, the ultrasound transducer 142 may be considered to be coupled to the infected inner surfaces in indirect contact established through the bodily tissues and any intervening bodily fluids, such as blood for example. As described above, one or both of the emitted energies may be continuous, pulsed, or any suitable combination thereof.

In treatment applications in which the surface being treated is living tissue, such as human tissue, the light energy (or other suitable form of electromagnetic energy) and the ultrasound energy (or other suitable form of mechanical stress energy) are each absorbed in total or in part by the targeted bacteria. Excess emitted energy may be absorbed by the tissue of the living host. In this regard, it will be appreciated that ultrasound energy may penetrate tissue to a greater depth than light energy, thereby making it desirable in certain applications to position an ultrasound emitting portion of a treatment device more remotely from the treatment surface than a corresponding light emitting portion.

Figure 15:
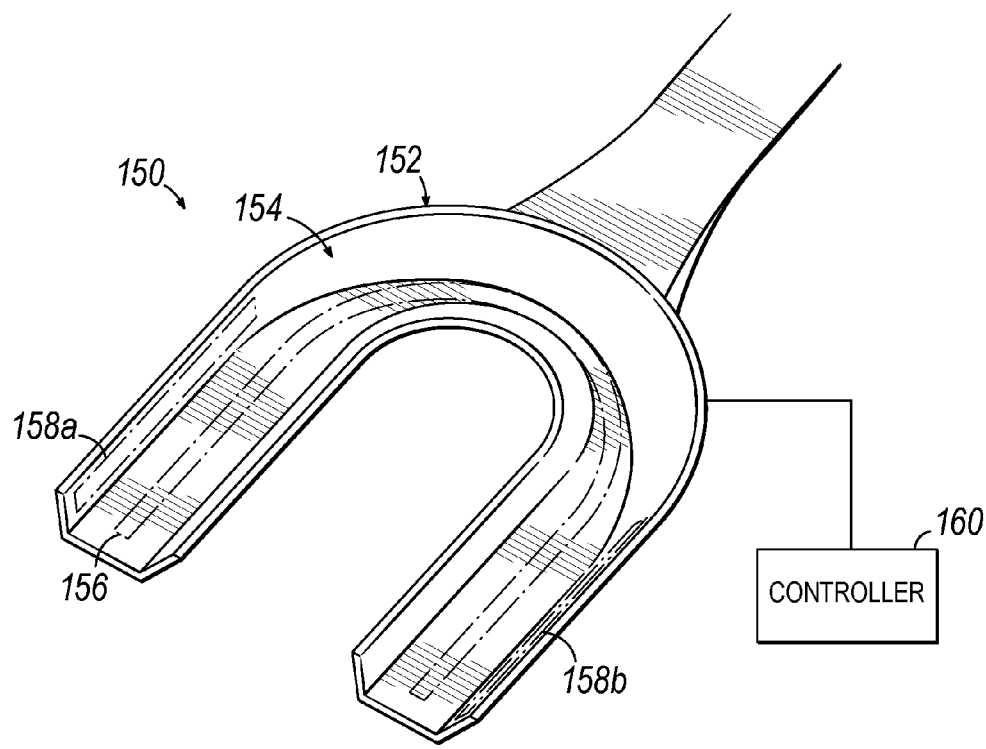
FIG. 15 is a schematic view of a photo-acoustic treatment device according to another embodiment of the invention.

With reference to FIG. 15, a photo-acoustic treatment device 150 according to another exemplary embodiment is shown for treatment of bacteria, including biofilms, residing on teeth of a patient. The treatment device 150 includes a device body 152 which may have a mouth guard like shape and an arch channel 154 for receiving an upper or lower dental arch of a user. The device body 152 may include a light emitting portion 156, which may be positioned adjacent to a crown portion of the dental arch, for example. The device body 152 may further include one or more ultrasound emitting portions, shown herein as emitting portions 158a and 158b, which may be positioned adjacent to opposing outer labial portions of the dental arch, for example. In one embodiment, a separate ultrasound transducer (not shown) may be positioned in direct or indirect contact with a surface of, or otherwise provided integrally within, the device body 152 at the location of the each of the ultrasound emitting portions 158a, 158b. Similarly, a light source (not shown) may be positioned adjacent a surface of, or otherwise provided integrally within, the device body 152 at the location of the light emitting portion 156.

A high viscosity gel may be provided in the arch channel 154 to establish indirect contact and maintain acoustic coupling between the ultrasound emitting portions 158a, 158b and the subject teeth during treatment. The light emitting portion 156 and the ultrasound emitting portions 158a, 158b may be coupled to a common controller 160 adapted to control application of combined ultrasound and light energies in a spatially overlapping manner and with energy characteristics similar to those described above.

In other embodiments, the treatment device 150 may include various alternative configurations and quantities of the light emitting portion 156 and the ultrasound emitting portions 158a, 158b, so as to achieve a desired treatment effect. Additionally, the device body 152 may be suitably shaped to closely conform to the curvature of the teeth, and thereby substantially directly contact the teeth being treated. In such embodiments, a thin layer of water or other fluid may be provided in the channel 154 to ensure acoustic coupling at regions of the ultrasound emitting portions 158a, 158b that may not directly contact the teeth. In one embodiment, the materials chosen for forming the device body 152 and any acoustic coupling medium may be transparent, translucent, or otherwise not unduly inhibiting of light transmission.

Figure 16:
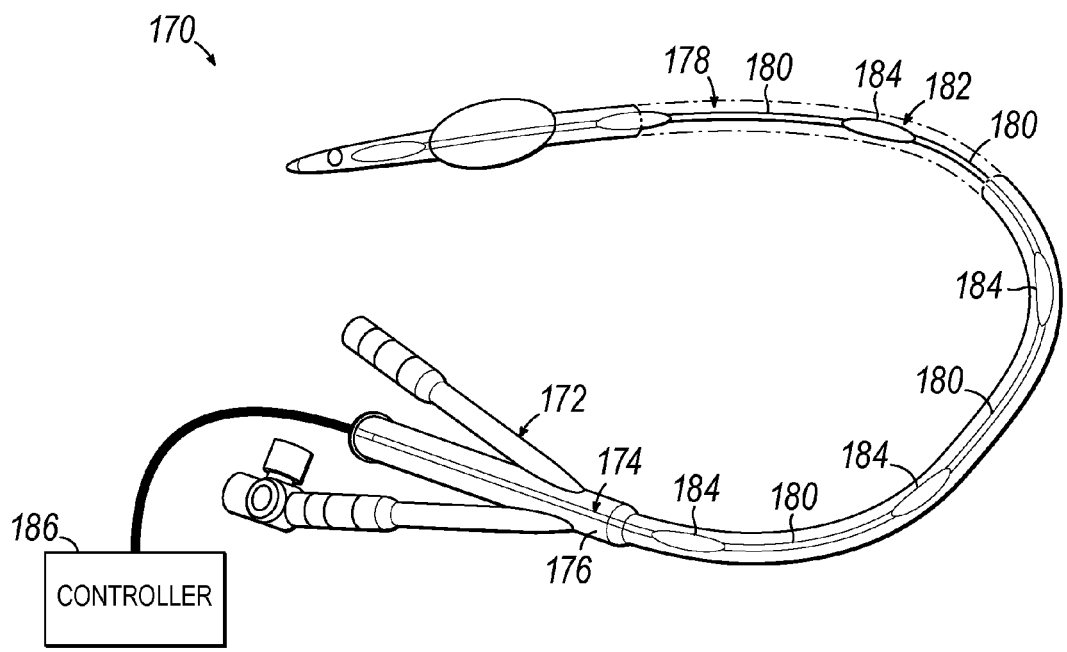
FIG. 16 is a schematic view of a photo-acoustic treatment device according to another embodiment of the invention.

With reference to FIG. 16, a photo-acoustic treatment device 170 according to another exemplary embodiment is shown for treatment of bacteria, including biofilms, residing on internal and external surfaces of a medical catheter 172. The catheter 172 may be of the type used for urine evacuation (e.g., a Foley catheter) or for nutrition and drug administration (e.g., a PICC line), for example. The treatment device 170 may include a device body 174 having an elongate, catheter-like or strand-like shape and being flexible for insertion through a lumen 176 of the medical catheter 172. The device body 174 may include a light emitting portion 178 having a plurality of axially spaced light emitting elements 180 operable to emit light. The device body 174 may further include an ultrasound emitting portion 182 having a plurality of axially spaced ultrasound emitting elements 184 alternatingly positioned between the light emitting elements 180 along the length of the device body 174, and operable to emit ultrasound. Each of the ultrasound emitting elements 184 may be formed with an outer diameter sufficiently large to directly contact, and thereby acoustically couple to, the radially inner surface of the catheter 172 defining the lumen 176. Alternatively, the ultrasound emitting elements 184 may be formed with diameters smaller than that of the radially inner surface of the catheter 172, and acoustic coupling may be established through indirect contact using an acoustic coupling medium, such as a viscous coupling fluid, for example.

In one embodiment, the ultrasound emitting elements 184 may include hollow cylinders or tubes, each housing a corresponding ultrasound transducer. The light emitting portion 178 may include an optical fiber (not shown) having a plurality of suitably spaced reflective elements forming the light emitting elements 180. Each of the light emitting elements 180 and the ultrasound emitting elements 184 may be configured to emit the respective energy from a full portion (i.e., 360 degrees) of its outer circumference. A proximal end of the device body 174 may be coupled to a controller 186 for controlling light and ultrasound emission from the energy emitting portions 178, 182.

In use, the device body 174 may be slowly inserted into and withdrawn from the catheter lumen 176, while the controller 186 controls the light emitting elements 180 and the ultrasound emitting elements 184 to emit their respective energies in a continuous manner, a pulsed manner, or a combination thereof. Thereby, a full length of the inner surface of the medical catheter 172 defining the lumen 176 may be exposed to combined light and ultrasound therapy for killing resident bacteria. In embodiments where the catheter 172 is formed of a material that does not unduly inhibit light transmission, light and ultrasound may pass radially outwardly through the wall of the catheter 172 to thereby treat bacteria residing on external surfaces of the catheter 172 as well. In this manner, the ultrasound emitting elements 184 may be considered to be coupled to the bacteria in indirect contact established through the wall of the catheter 172, and through any acoustic coupling fluid provided between the wall and the ultrasound emitting elements 184.

As shown, the device body 174 may be an integral, unitary structure including both the light emitting portion 178 and ultrasound emitting portion 182, thereby enabling delivery of both light and ultrasound energy internally in a radially outward direction. In an alternative embodiment, the light emitting portion 178 may be formed separately from the ultrasound emitting portion 182. Accordingly, the light emitting portion 178 may be positioned internally and deliver light in a radially outward direction, while the ultrasound emitting portion 182 may be positioned externally and deliver ultrasound in a direction radially inward in a manner similar to that described above in connection with the embodiment of FIG. 14, for example.

A treatment device of the configuration described above, having independently formed light and ultrasound emitting portions, may be used for treatment of a portion of a catheter 172 that remains surgically positioned within a patient. In particular, the light emitting portion may be inserted into the catheter lumen 176 to emit light onto a radially inner surface of the lumen 176. The independently formed ultrasound emitting portion may be positioned extracorporeally in coupling engagement with the outer skin of the patient at a location generally overlying the portion of the catheter 172 to be treated. The ultrasound emitting portion may then transmit ultrasound energy through the outer skin and intervening bodily tissues in a direction toward the portion of the catheter 172 to be treated, and through the catheter wall to reach the radially inner surface receiving the light (e.g., in a manner similar to that shown in FIG. 14). In this manner, bacteria residing on the radially inner surface of the catheter 172 may be treated with combined light and ultrasound energies. When the cannula wall is formed of a material conducive to light transmission, the light emitted by the light emitting portion may also reach bacteria residing on radially outer surfaces the catheter 172, along with ultrasound transmitted extracorporeally by the separate ultrasound emitting portion. In this regard, the ultrasound emitting portion of the treatment device is coupled to the bacteria on the catheter 172 in indirect contact established through the skin and other intervening bodily tissues positioned between the catheter 172 and the ultrasound emitting portion. Where treatment of radially inner surfaces of the catheter 172 is achieved, the indirect contact is further established through the wall of the catheter 172.

In another embodiment of treating catheters with combined mechanical stress energy and electromagnetic energy, the ultrasound emitting portion 182 may be omitted from the treatment device. The device body 174, including the light emitting portion 178, may be inserted into the catheter lumen 176 and vibrated such that the device body 174 radiates vibrational energy radially outward along the length of the device body 174. Such an embodiment may be particularly advantageous due to the elimination of wires otherwise extending from the ultrasound emitting portion 182. The vibrational energy delivered to the device body 174 may include longitudinal, transverse, and/or rotational/torsional movements, for example. In a similar alternative embodiment, the device body 174 may be held stationary within the catheter lumen 176 while the catheter 172 is vibrated relative to the device body 174.

In furtherance of the methods described above for treating a medical catheter, it will be appreciated that the bacteria treatment methods disclosed herein may be adapted as appropriate for treating other non-living surfaces as well. As discussed above, bacterial biofilms often grow on non-living surfaces in industrial or marine environments, for example on boat hulls or piping. In such cases, treatments may be delivered with ultrasound and light of generally higher intensities without concern for harming living tissue. Additionally, the combined mechanical stress energy and electromagnetic energy treatment methods disclosed herein may be adapted for treating non-bacterial biofilms.

Moreover, while the methods for treating bacteria disclosed herein describe application of combined ultrasound and light energies, any suitable combination of mechanical stress energy and electromagnetic energy may be used. Mechanical stress energy may include sound energy or other forms of vibration energy generated as a result of a structure experiencing a mechanical stress, for example. Electromagnetic energy may include all known forms of electromagnetic radiation along the electromagnetic spectrum, including visible light and X rays, for example.

Figure 17:
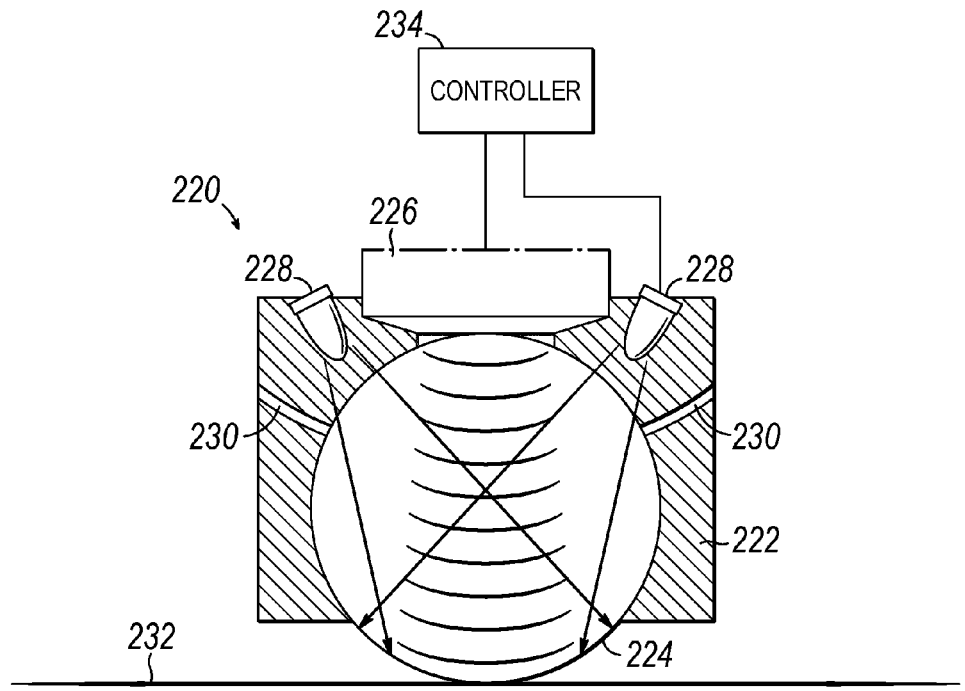
FIG. 17 is a schematic view of a photo-acoustic treatment device according to another embodiment of the invention.

With reference to FIG. 17, a photo-acoustic treatment device 220 according to another exemplary embodiment is shown for treatment of bacteria with combined mechanical stress energy and electromagnetic energy. The treatment device 220 may include a device body 222 that at least partially houses a photo-acoustic rolling element 224. The photo-acoustic rolling element 224 may rotate relative to the device body 222 as the rolling element 224 contacts (e.g., tangentially) and rolls across a treatment surface 232 (e.g., the skin of a patient), for example when the treatment device 220 is traversed across the treatment surface 232 under a traversing force applied by a user. In one embodiment, the photo-acoustic rolling element 224 may be cylindrically shaped and formed of an acrylic material, similar to the photo-acoustic element 46 described above in connection with FIGS. 1 and 2. In other embodiments, the photo-acoustic rolling element 224 may be of any other suitable shape and formed of a material conducive to ultrasound and light transmission. For example, in one embodiment, the rolling element 224 may be in the form of a sphere that enables movements of the treatment device 220 along two separate axes (e.g., X and Y) on a plane defined by the treatment surface 232.

The treatment device 220 further includes an ultrasound transducer 226 and one or more light sources 228, which may be coupled to the device body 222 and supported above the photo-acoustic rolling element 224. The ultrasound transducer 226 may directly or indirectly contact the rolling element 224, for example through an acoustic coupling fluid, for transmission of ultrasound energy. In a manner similar to that described above in connection with treatment devices 12, 12a of FIGS. 1A-2, ultrasound and light energies emitted by the ultrasound transducer 226 and the light sources 228 may be transmitted through the rolling element 224 and onto a treatment surface 232 as the treatment device 220 is traversed across the treatment surface 232. For example, as shown in FIG. 17, ultrasound energy may be transmitted diametrically through the rolling element 224, and light energy may be transmitted angularly through the rolling element 224, onto the treatment surface 232 as the rolling element 224 rotates about is central axis. At least a portion of the rolling element 224 may protrude from the device body 222 for contacting the treatment surface 232.

The device body 222 may include one or more fluid ducts 230 for providing a flow of acoustic coupling fluid onto an outer surface of the rolling element 224 during rotation. The acoustic coupling fluid may aid in maintaining acoustic coupling between the ultrasound transducer 226 and the rolling element 224, and between the rolling element 224 and the treatment surface 232. Accordingly, the rolling element 224 may directly contact the treatment surface 232 at a tangential region, and may furthermore indirectly contact the treatment surface 232, through the acoustic coupling fluid, at a pair of opposed regions on either side of and circumferentially spaced from the tangential region. The ultrasound transducer 226 may be considered to be coupled to bacteria on the treatment surface 232 in indirect contact established through the rolling element 224, and through any acoustic coupling fluid provided between the transducer 226 and the rolling element 224 and between the rolling element 224 and the treatment surface 232. The ultrasound transducer 226 and light sources 228 may be controlled by a controller 234 to provide combined ultrasound and light energies to bacteria on the treatment surface 232 in manners, and with emission parameters, as generally described above.

Figure 18:
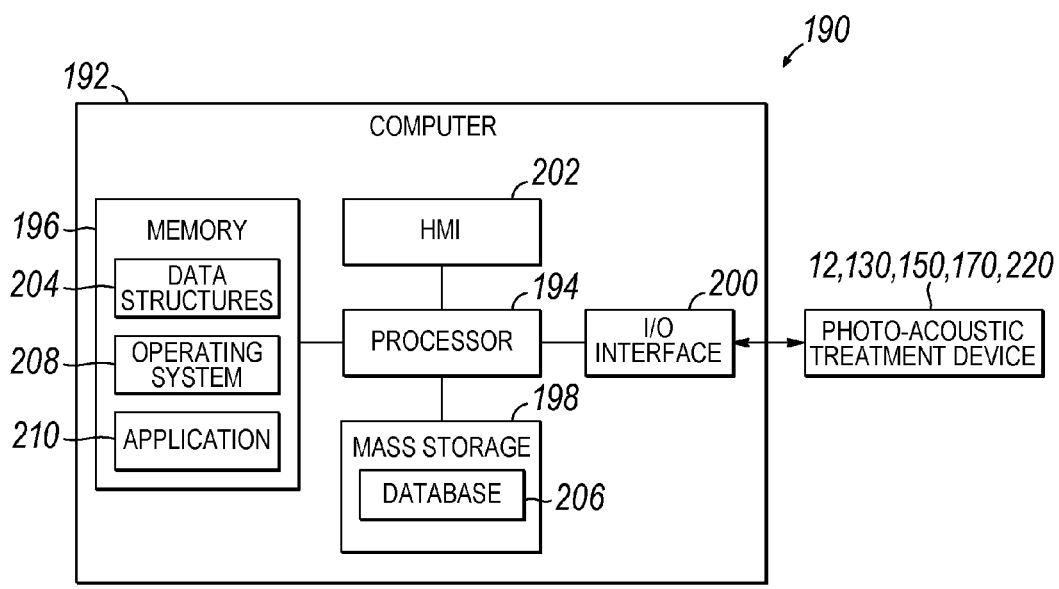
FIG. 18 is a diagrammatic view of a control system for controlling a photo-acoustic treatment device to expose bacteria to light and ultrasound according to an embodiment of the invention.

With reference to FIG. 18, any one or multiple of the photo-acoustic treatment devices 12, 12a, 130, 150, 170, and 220 may comprise part of a treatment system 190 that includes a controller implemented on one or more computing devices or systems (collectively referred to herein as a computer), such as computer 192. The computer 192 may include at least one processor 194, a memory 196, a mass storage memory device 198, an input/output (I/O) interface 200, and a Human Machine Interface (HMI) 202. The computer 192 may also be operatively coupled to one or more external resources via a network and/or the I/O interface 200. External resources may include, but are not limited to, servers, databases, mass storage devices, peripheral devices, cloud-based network services, or any other suitable computing resource that may be used by the computer 192.

The processor 194 may include one or more devices selected from microprocessors, micro-controllers, digital signal processors, microcomputers, central processing units, field programmable gate arrays, programmable logic devices, state machines, logic circuits, analog circuits, digital circuits, or any other device that manipulates signals (analog or digital) based on operational instructions that are stored in the memory 196. The memory 196 may include a single memory device or a plurality of memory devices including, but not limited to, read-only memory (ROM), random access memory (RAM), volatile memory, non-volatile memory, static random access memory (SRAM), dynamic random access memory (DRAM), flash memory, cache memory, or any other device capable of storing data. The mass storage memory device 198 may include data storage devices such as a hard drive, optical drive, tape drive, non-volatile solid state device, or any other device capable of storing data.

The processor 194 may operate under the control of an operating system 208 that resides in the memory 196. The operating system 208 may manage computing resources so that computer program code embodied as one or more computer software applications, such as an application 210 resident in the memory 196, may have its instructions executed by the processor 194. Alternatively, the processor 194 may execute the application 210 directly, in which circumstance the operating system 208 may be omitted. One or more data structures 204 may also reside in the memory 196, and may be used by the processor 194, operating system 208, or application 210 to store or manipulate data.

The I/O interface 200 may provide a machine interface that operatively couples the processor 194 to the photo-acoustic treatment device 12, 12a, 130, 150, 170, 220. The application 210 may thereby work cooperatively with the photo-acoustic treatment device 12, 12a, 130, 150, 170, 220 by communications and/or signals supplied over the I/O interface 200 to provide the various features, functions, or processes comprising embodiments of the invention. The application 210 may also have program code that is executed by one or more external resources, or otherwise rely on functions or signals provided by other system or network components external to the computer 192. Indeed, given the nearly endless hardware and software configurations possible, a person of ordinary skill in the art will understand that applications and databases may be located externally to the computer 192, distributed among multiple computers or other external resources, or provided by computing resources (hardware and software) that are provided as a service over a network, such as a cloud computing service.

The HMI 202 may be operatively coupled to the processor 194 of computer 192 in a known manner to allow a user to interact directly with the computer 192. The HMI 202 may include video or alphanumeric displays, a touch screen, a speaker, and any other suitable audio and visual indicators capable of providing data to the user. The HMI 202 may also include input devices and controls such as an alphanumeric keyboard, a pointing device, keypads, pushbuttons, control knobs, microphones, etc., capable of accepting commands or input from the user and transmitting the entered input to the processor 194.

A database 206 may reside on the mass storage memory device 198, and may be used to collect and organize data used by the treatment system, such as data providing recipes for procedures to expose a biofilm to light and sound. The database 206 may include data and supporting data structures that store and organize the data. In particular, the database 206 may be arranged with any database organization or structure including, but not limited to, a relational database, a hierarchical database, a network database, or combinations thereof. A database management system in the form of a computer software application executing as instructions on the processor 194 may be used to access the information or data stored in records of the database 206 in response to the initiation of a procedure to expose a biofilm to light and sound.

In general, the routines executed to implement the embodiments of the invention, whether implemented as part of an operating system or a specific application, component, program, object, module or sequence of instructions, or even a subset thereof, will be referred to herein as "computer program code," or simply "program code." Program code typically comprises one or more instructions that are resident at various times in various memory and storage devices in a computer, and that, when read and executed by one or more processors in a computer, cause that computer to perform the steps necessary to execute steps or elements embodying the various aspects of the invention. Moreover, while the invention has and hereinafter will be described in the context of fully functioning computers and computer systems, those skilled in the art will appreciate that the various embodiments of the invention are capable of being distributed as a program product in a variety of forms, and that the invention applies equally regardless of the particular type of computer readable media used to actually carry out the distribution.

The program code embodied in any of the applications/modules described herein is capable of being individually or collectively distributed as a program product in a variety of different forms. In particular, the program code may be distributed using a computer readable media, which may include computer readable storage media and communication media. Computer readable storage media, which is inherently non-transitory, may include volatile and non-volatile, and removable and non-removable tangible media implemented in any method or technology for storage of information, such as computer-readable instructions, data structures, program modules, or other data. Computer readable storage media may further include RAM, ROM, erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer. Communication media may embody computer readable instructions, data structures or other program modules. By way of example, and not limitation, communication media may include wired media such as a wired network or direct-wired connection, and wireless media such as acoustic, RF, infrared and other wireless media. Combinations of any of the above may also be included within the scope of computer readable media.

These computer program instructions may also be stored in a computer readable medium that can direct a computer, other types of programmable data processing apparatus, or other devices to function in a particular manner, such that the instructions stored in the computer readable medium may implement a particular function or act.

The computer program instructions may also be loaded onto a computer, other programmable data processing apparatus, or another device to cause a series of computations to be performed on the computer, the other processing apparatus, or the other device to produce a computer implemented process such that the executed instructions provide one or more processes for implementing a particular function or act.

The terminology used herein is for the purpose of describing particular embodiments only and is not intended to be limiting of the embodiments of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes," "having," "has," "with," "comprised of," or variants thereof are used in either the detailed description or the claims, such terms are intended to be inclusive in a manner similar to the term "comprising".

While the present invention has been illustrated by a description of various embodiments and while these embodiments have been described in considerable detail, it is not the intention of the Applicant to restrict or in any way limit the scope of the appended claims to such detail. Additional advantages and modifications will readily appear to those skilled in the art. The invention in its broader aspects is therefore not limited to the specific details, representative apparatus and method, and illustrative examples shown and described. Accordingly, departures may be made from such details without departing from the spirit or scope of the Applicant's general inventive concept.

What is claimed is:

1. A method for treating bacteria, the method comprising:
coupling a portion of a treatment device with the bacteria through direct or indirect contact;
generating ultrasound with the treatment device;
generating electromagnetic energy with the treatment device;
transmitting the ultrasound and the electromagnetic energy from the treatment device to the bacteria during the coupling with the bacteria; and
treating the bacteria with both the ultrasound and the electromagnetic energy generated by the treatment device to produce a killing effect on the bacteria,
wherein the ultrasound is transmitted with an averaged sound intensity greater than or equal to 10 mW/cm$^2$ and less than or equal to 1 W/cm$^2$, and the ultrasound is transmitted with a pressure amplitude at the bacteria greater than or equal to 50 kPa and less than or equal to 1 MPa.

2. The method of claim 1, wherein transmitting the ultrasound and the electromagnetic energy further comprises:
transmitting at least one of the ultrasound or the electromagnetic energy from the portion of the treatment device coupled through the direct or indirect contact with the bacteria.

3. The method of claim 1, wherein treating the bacteria includes spatially overlapping the ultrasound and the electromagnetic energy at the location of the bacteria being treated to enhance the killing effect.

4. The method of claim 1, wherein treating the bacteria includes pulsing at least one of the ultrasound or the electromagnetic energy.

5. The method of claim 4, wherein the at least one of the ultrasound or the electromagnetic energy is pulsed with a pulse repetition interval greater than or equal to 1 ms and less than or equal to 100 ms.

6. The method of claim 4, wherein the at least one of ultrasound or the electromagnetic energy is pulsed with a pulse duration greater than or equal to 100 μs and less than or equal to 2 ms.

7. The method of claim 4, wherein treating the bacteria includes temporally alternating and interleaving the ultrasound and the electromagnetic energy.

8. The method of claim 4, wherein treating the bacteria includes at least partially temporally overlapping the ultrasound and the electromagnetic energy.

9. The method of claim 1, wherein the ultrasound is transmitted with a frequency greater than or equal to 20 kHz and less than or equal to 5 MHz.

10. The method of claim 1, wherein the ultrasound is transmitted with a duty cycle greater than or equal to 1.1 percent and less than or equal to 11 percent.

11. The method of claim 1, wherein the electromagnetic energy includes light, and transmitting the electromagnetic energy includes transmitting the light.

12. The method of claim 11, wherein the light is transmitted with a wavelength greater than or equal to 400 nm and less than or equal to 450 nm.

13. The method of claim 11, wherein the light is transmitted with a wavelength greater than or equal to 500 nm and less than or equal to 660 nm.

14. The method of claim 11, wherein the light is transmitted with a duty cycle greater than or equal to 2 percent and less than or equal to 100 percent.

15. The method of claim 11, wherein the light is transmitted with an averaged light intensity greater than or equal to 5 mW/cm$^2$ and less than or equal to 500 mW/cm$^2$.

16. The method of claim 1, wherein the bacteria includes a biofilm, and treating the bacteria includes treating the biofilm.

17. The method of claim 1, wherein the bacteria includes planktonic bacteria, and treating the bacteria includes treating the planktonic bacteria.

* * * * *